(12) United States Patent
Vogels et al.

(10) Patent No.: US 7,820,440 B2
(45) Date of Patent: Oct. 26, 2010

(54) MEANS AND METHODS FOR PRODUCING ADENOVIRUS VECTORS

(75) Inventors: Ronald Vogels, Linschoten (NL); Abraham Bout, Moerkapelle (NL)

(73) Assignee: Crucell Holland B.V., Leiden (NL)

( * ) Notice: Subject to any disclaimer, the term of this patent is extended or adjusted under 35 U.S.C. 154(b) by 260 days.

(21) Appl. No.: 11/800,871

(22) Filed: May 7, 2007

(65) Prior Publication Data

US 2008/0199917 A1 Aug. 21, 2008

Related U.S. Application Data

(62) Division of application No. 10/512,589, filed as application No. PCT/EP03/50125 on Apr. 24, 2003, now Pat. No. 7,468,181.

(30) Foreign Application Priority Data

Apr. 25, 2002 (WO) .................... PCT/NL02/00280

(51) Int. Cl.
C12N 15/861 (2006.01)
C12N 15/63 (2006.01)
C12N 15/11 (2006.01)
C12N 15/00 (2006.01)
C12N 15/34 (2006.01)
C12N 5/00 (2006.01)

(52) U.S. Cl. .................... 435/456; 435/325; 435/371; 435/320.1; 435/455; 536/23.72; 536/24.1; 424/93.2

(58) Field of Classification Search .................... None
See application file for complete search history.

(56) References Cited

U.S. PATENT DOCUMENTS

| | | | |
|---|---|---|---|
| 4,487,829 A | 12/1984 | Sharp et al. |
| 4,517,686 A | 5/1985 | Ruoslahti et al. |
| 4,578,079 A | 3/1986 | Ruoslahti et al. |
| 4,589,881 A | 5/1986 | Pierschbacher et al. |
| 4,593,002 A | 6/1986 | Dulbecco |
| 4,792,525 A | 12/1988 | Ruoslahti et al. |
| 4,797,368 A | 1/1989 | Carter et al. |
| 4,956,281 A | 9/1990 | Wallner et al. |
| 5,024,939 A | 6/1991 | Gorman |
| 5,096,815 A | 3/1992 | Ladner et al. |
| 5,166,320 A | 11/1992 | Wu et al. |
| 5,198,346 A | 3/1993 | Ladner et al. |
| 5,204,445 A | 4/1993 | Plow et al. |
| 5,223,394 A | 6/1993 | Wallner |
| 5,223,409 A | 6/1993 | Ladner et al. |
| 5,240,846 A | 8/1993 | Collins et al. |
| 5,246,921 A | 9/1993 | Reddy et al. |
| 5,332,567 A | 7/1994 | Goldenberg |
| 5,349,053 A | 9/1994 | Landolfi |
| 5,403,484 A | 4/1995 | Ladner et al. |
| 5,436,146 A | 7/1995 | Shenk et al. |
| 5,443,953 A | 8/1995 | Hansen et al. |
| 5,474,935 A | 12/1995 | Chatterjee et al. |
| 5,521,291 A | 5/1996 | Curiel et al. |
| 5,534,423 A | 7/1996 | Plasson et al. |
| 5,543,328 A | 8/1996 | Mcclelland et al. |
| 5,547,932 A | 8/1996 | Curiel et al. |
| 5,552,311 A | 9/1996 | Sorscher et al. |
| 5,559,099 A | 9/1996 | Wickham et al. |
| 5,571,698 A | 11/1996 | Ladner et al. |
| 5,622,699 A | 4/1997 | Ruoslahti et al. |
| 5,698,443 A | 12/1997 | Henderson et al. |
| 5,712,136 A | 1/1998 | Wickham et al. |
| 5,731,190 A | 3/1998 | Wickham et al. |
| 5,756,086 A | 5/1998 | Mcclelland et al. |
| 5,770,442 A | 6/1998 | Wickham et al. |
| 5,837,511 A | 11/1998 | Falck-Pedersen et al. |
| 5,846,782 A | 12/1998 | Wickham et al. |
| 5,849,561 A | 12/1998 | Falck-Pedersen |
| 5,856,152 A | 1/1999 | Wilson et al. |
| 5,871,726 A | 2/1999 | Henderson et al. |
| 5,871,727 A | 2/1999 | Curiel |
| 5,871,982 A | 2/1999 | Wilson et al. |
| 5,877,011 A | 3/1999 | Armentano et al. |
| 5,922,315 A | 7/1999 | Roy |
| 5,981,275 A | 11/1999 | Armentano et al. |

(Continued)

FOREIGN PATENT DOCUMENTS

EP 259212 8/1987

(Continued)

OTHER PUBLICATIONS

Abrahamsen et al., "Construction of an Adenovirus Type 7a E1A-Vector," Journal of Virology, Nov. 1997, p. 8946-8951 vol. 71, No. 11.
Albiges-Rizo et al., "Human Adenovirus Serotype 3 Fiber Protein," Journal of Biological Chemistry, 266(6), 3961 3967 (1991).
Anderson, Nature, "Human gene therapy," Apr. 1998, pp. 25-30, vol. 392.
Athappilly et al., "The Refined Crystal Structure of Hexon, the Major Coat Protein of Adenovirus Type 2, at 2-9 A Resolution," J. Mol. Biol. (1994) 242, 430-455.
Bai et al., "Mutations That Alter an Arg-Gly-Asp (RGD) Sequence in the Adenovirus Type 2 Penton Base Protein Abolish Its Cell-Rounding Activity and Delay Virus Reproduction in Flat Cells," Journal of Virology, 67(9), 5198 5205 (1993).

(Continued)

Primary Examiner—Maria Marvich
(74) Attorney, Agent, or Firm—TraskBritt

(57) ABSTRACT

The invention relates to methods and means for producing adenoviral vectors on complementing cell lines, wherein the early region 4 open reading frame 6 (E4-orf6) encoding nucleic acid is present in the adenoviral vector and wherein the E4-orf6 gene product is compatible with one or more products of the E1 gene products provided by the complementing cell, such that the adenoviral vector can be efficiently produced by the complementing cell.

23 Claims, 19 Drawing Sheets

U.S. PATENT DOCUMENTS

| | | | |
|---|---|---|---|
| 5,994,128 | A | 11/1999 | Fallaux et al. |
| 6,007,806 | A | 12/1999 | Lathe et al. |
| 6,033,908 | A | 3/2000 | Bout et al. |
| 6,057,155 | A | 5/2000 | Wickham et al. |
| 6,057,299 | A | 5/2000 | Henderson |
| 6,100,086 | A | 8/2000 | Kaplan et al. |
| 6,127,525 | A | 10/2000 | Crystal et al. |
| 6,287,857 | B1 | 9/2001 | O'riordan et al. |
| 6,306,652 | B1 | 10/2001 | Fallaux et al. |
| 6,358,507 | B1 | 3/2002 | Kaplan et al. |
| 6,417,168 | B1 * | 7/2002 | Greene et al. ............. 514/44 |
| 6,486,133 | B1 | 11/2002 | Herlyn et al. |
| 6,492,169 | B1 | 12/2002 | Vogels et al. |
| 6,632,427 | B1 | 10/2003 | Finiels et al. |
| 6,669,942 | B2 | 12/2003 | Perricaudet et al. |
| 6,844,192 | B2 | 1/2005 | Orlando et al. |
| 6,913,922 | B1 | 7/2005 | Bout et al. |
| 6,974,695 | B2 * | 12/2005 | Vogels et al. ............. 435/325 |
| 7,270,811 | B2 | 9/2007 | Bout et al. |
| 7,285,265 | B2 * | 10/2007 | Vogels et al. ............. 424/93.2 |
| 7,300,657 | B2 | 11/2007 | Pau et al. |
| 7,468,181 | B2 * | 12/2008 | Vogels et al. ............. 424/93.2 |
| 2002/0028194 | A1 | 3/2002 | Kaplan et al. |
| 2002/0052485 | A1 | 5/2002 | Colosi |
| 2003/0026783 | A1 | 2/2003 | Abina |
| 2003/0044383 | A1 | 3/2003 | Henderson et al. |
| 2003/0152553 | A1 | 8/2003 | Little et al. |
| 2005/0196384 | A1 | 9/2005 | Vogels et al. |
| 2005/0244381 | A1 | 11/2005 | Mallet et al. |
| 2007/0010016 | A1 | 1/2007 | McCelland et al. |
| 2007/0041946 | A1 | 2/2007 | Bout et al. |

FOREIGN PATENT DOCUMENTS

| | | |
|---|---|---|
| EP | 1016726 | 12/1998 |
| EP | 99201545.3 | 5/1999 |
| EP | 1067188 | 7/1999 |
| EP | 1020529 | 11/1999 |
| EP | 0 978 566 A2 | 2/2000 |
| EP | 1 054 064 A1 | 11/2000 |
| WO | WO 91/00360 | 1/1991 |
| WO | WO 91/05805 | 5/1991 |
| WO | WO 91/05871 | 5/1991 |
| WO | WO 92/02553 | 2/1992 |
| WO | WO 92/13081 | 8/1992 |
| WO | WO 93/03769 | 3/1993 |
| WO | WO 93/06223 | 4/1993 |
| WO | WO 93/07282 | 4/1993 |
| WO | WO 93/07283 | 4/1993 |
| WO | WO 94/08026 | 4/1994 |
| WO | WO 94/10323 | 5/1994 |
| WO | WO 94/11506 | 5/1994 |
| WO | WO 94/15644 | 7/1994 |
| WO | WO 94/17832 | 8/1994 |
| WO | WO 94/24299 | 10/1994 |
| WO | WO 94/26915 | 11/1994 |
| WO | WO 95/05201 | 2/1995 |
| WO | WO 95/06745 | 3/1995 |
| WO | WO 95/14785 | 6/1995 |
| WO | WO 95/16037 | 6/1995 |
| WO | WO 95/21259 | 8/1995 |
| WO | WO 95/26412 | 10/1995 |
| WO | WO 95/27071 | 10/1995 |
| WO | WO 95/31187 | 11/1995 |
| WO | WO 95/31566 | 11/1995 |
| WO | WO 96/00326 | 1/1996 |
| WO | WO 96/00790 | 1/1996 |
| WO | WO 96/07739 | 3/1996 |
| WO | WO 96/10087 | 4/1996 |
| WO | WO 96/12030 | 4/1996 |
| WO | WO 96/13597 | 5/1996 |
| WO | WO 96/13598 | 5/1996 |
| WO | WO 96/14837 | 5/1996 |
| WO | WO 96/17073 | 6/1996 |
| WO | WO 96/18740 | 6/1996 |
| WO | WO 96/24453 | 8/1996 |
| WO | WO 96/26281 | 8/1996 |
| WO | WO 96/35798 | 11/1996 |
| WO | WO 97/00326 | 1/1997 |
| WO | WO 97/01358 | 1/1997 |
| WO | WO 97/12986 | 4/1997 |
| WO | WO 98/22609 | 4/1997 |
| WO | WO 97/20575 | 6/1997 |
| WO | WO 97/38723 | 10/1997 |
| WO | WO 98/01563 | 1/1998 |
| WO | WO 98/07865 | 2/1998 |
| WO | WO 98/11221 | 3/1998 |
| WO | WO 98/13499 | 4/1998 |
| WO | WO 98/32842 | 7/1998 |
| WO | WO 98/40509 | 9/1998 |
| WO | WO 98/46779 | 10/1998 |
| WO | WO 98/46781 | 10/1998 |
| WO | WO 98/49300 | 11/1998 |
| WO | WO 98/50053 A1 | 11/1998 |
| WO | WO 98/53087 | 11/1998 |
| WO | WO 99/32647 | 7/1999 |
| WO | WO 99/47180 A1 | 9/1999 |
| WO | WO 99/55132 | 11/1999 |
| WO | WO 99/58646 | 11/1999 |
| WO | WO 99/61640 | 12/1999 |
| WO | WO 00/03029 | 1/2000 |
| WO | WO 00/24730 A2 | 5/2000 |
| WO | WO 00/29573 | 5/2000 |
| WO | WO 00/31285 | 6/2000 |
| WO | WO 00/52186 | 9/2000 |
| WO | WO 00/70071 A1 | 11/2000 |
| WO | WO 01/04334 | 1/2001 |
| WO | WO 01/83797 | 11/2001 |
| WO | WO 01/90158 A1 | 11/2001 |
| WO | WO 02/24730 | 3/2002 |
| WO | WO 02/27006 | 4/2002 |

OTHER PUBLICATIONS

Bailey et al., "Phylogenetic Relationships among Adenovirus Serotypes," Virology, 205, 439 452 (1994).

Ball-Goodrich et al., "Parvoviral Target Cell Specificity: Acquisition of Fibrotropism by a Mutant of the Lymphotropic Strain of Minute Virus of Mice Involves Multiple Amino Acid Substitutions within the Capsid," Virology, 184, 175 186 (1991). Abstract.

Basler et al., "Subgroup B Adenovirus Type 35 Early Region 3 mRNAs Differ from Those of the Subgroup C Adenoviruses," Virology 215, 165-177 (1996).

Basler et al., Sequence of the immunoregulatory early region 3 and flanking sequences of adenovirus type 35, 1996, pp. 249-254, Gene, vol. 170.

Batra et al., "Receptor-mediated gene delivery employing lectin-binding specificity," Gene Therapy, 1, 255 260 (1994).

Berendsen, Herman J.C., A Glimpse of the Holy Grail, Science, 1998, vol. 282, pp. 642-643.

Boursnell et al., "In vitro construction of a recombinant adenovirus Ad2:Ad5," Gene, 13, 311-317 (1981).

Bridge et al., "Adenovirus Early Region 4 and Viral DNA Synthesis," Virology 193, 794-801 (1993).

Brody et al., "Adenovirus-Mediated in Vivo Gene Transfer," Annals New York Academy of Sciences pp. 90-100.

Caillet-Boudin et al., "Functional and Structural Effects of an Ala to Val Mutation in the Adenovirus Serotype 2 Fibre," J. Mol. Biol., 217, 477-486 (1991).

Chiu et al., Folding & Design, "Optimizing energy potentials for success in protein tertiary structure prediction," May 1998, pp. 223-228, vol. 3.

Chroboczek et al., "The Sequence of the Genome of Adenovirus Type 5 and Its Comparison with the Genome of Adenovirus Type 2," Virology, 186, 280-285 (1992).
Chroboczek et al., Adenovirus Fiber, Current Topics in Microbiology and Immunology 1995;199 (Pt 1) pp. 163-200.
Chu et al., "Cell targeting with retroviral vector particles containing antibody-envelope fusion proteins," Gene Therapy, I, 292-299 (1994). Abstract.
Cotten et al., "High-efficiency receptor-mediated delivery of small and large (48 kilobase gene constructs using the endosome-disruption activity of defective or chemically inactivated adenovirus particles," Proc. Natl. Acad. Sci. USA, 89, 6094-6098 (1992).
Cotten et al., "Transferrin-polycation-mediated introduction of DNA into human leukemic cells: Stimulation by agents that affect the survival of transfected DNA or modulate transferrin receptor levels," Proc. Natl. Acad. Sci. USA, 87, 4033-4037 (1990).
Crawford-Miksza et al., "Analysis of 15 Adenovirus Hexon Proteins Reveals the Location and Structure of Seven Hypervariable Regions Containing Serotype-Specific Residues," Journal of Virology, Mar. 1996, p. 1836-1844.
Crompton et al., "Expression of a foreign epitope on the surface of the adenovirus hexon," J. Gen. Virol., 75(1), 133-139 (1994).
Crystal, Ronald G., "Transfer of Genes to Humans: Early Lessons and Obstacles to Success," Science, 270, 404-410 (1995).
Curiel et al., "Adenovirus enhancement of transferring-polylysine-mediated gene delivery," Proc. Natl. Acad. Sci. USA, 88, 8850-8854 (1991).
Curiel et al., "High-Efficiency Gene Transfer Mediated by Adenovirus Coupled to DNABPolylysine Complexes," Human Gene Therapy, 3, 147-154 (1992). Abstract.
De Jong et al., "Adenovirus Isolates From Urine of Patients with Acquired Immunodeficiency Syndrome," The Lancet, Jun. 11, 1983 pp. 1293-1296.
De Jong et al., Adenoviruses from Human Immunodeficiency Virus-Infected Individuals, Including Two Strains That Represent New Candidate Serotypes Ad50 and Ad51 of Species B1 and D, Respectively, Journal of Clinical Microbiology, Dec. 1999, p. 3940-45, vol. 37, No. 12, American Society for Microbiology.
Defer et al., "Human Adenovirus-Host Cell Interactions: Comparative Study with Members of Subgroups B and C," Journal of Virology, 64(8), 3661-3673 (1990).
Deonarain, "Ligand-targeted receptor-mediated vectors for gene delivery," (1998) Expert Opin. Ther. Pat. 8: 53-69.
Dijkema et al., "Transformation of Primary Rat Kidney Cells by DNA Fragments of Weakly Oncogenic Adenoviruses," Journal of Virology, Dec. 1979, p. 943-950.
Douglas J T et al.: "Strategies to accomplish targeted gene delivery to muscle cells employing tropism-modified adenoviral vectors" Neuromusclar Disorders, Pergamon Press, GB, vol. 7, Jul. 1997, pp. 284-298, XP002079944 ISSN: 0960-8966. Abstract.
Dupuit et al., "Regenerating Cells in Human Airway Surface Epithelium Represent Preferential Targets for Recombinant Adenovirus," Human Gene Therapy, 6, 1185-1193 (1995). Abstract.
Eck et al., "Gene-Based Therapy," (1996) Goodman & Gillman's The Pharmacological Basis of Therapeutics, Mc-Graw-Hill, New York, N.Y., pp. 77-101.
Etienne-Julan et al., "The efficiency of cell targeting by recombinant retroviruses depends on the nature of the receptor and the composition of the artificial cell-virus linker," Journal of General Virology, 73, 3251-3255 (1992). Abstract.
Falgout et al., "Characterization of Adenovirus Particles Made by Deletion Mutants Lacking the Fiber Gene," Journal of Virology, 62(2), 622-625 (1988).
Flomenberg et al., "Molecular Epidemiology of Adenovirus Type 35 Infections in Immunocompromised Hosts," The Journal of Infectious Diseases vol. 155, No. 6, Jun. 1987.
Francki et al., "Classification and Nomenclature of Viruses," Fifth Report of the International Committee on Taxonomy of Viruses; Virology Division of the International Union of Microbiology Societies pp. 140-143.

Gall et al., "Adenovirus Type 5 and 7 Capsid Chimera: Fiber Replacement Alters Receptor Tropism without Affecting Primary Immune Neutralization Epitopes," Journal of Virology, Apr. 1996, p. 2116-2123.
Gall et al., "Construction and characterization of Hexon-Chimeric Adenoviruses: Specification of adenovirus serotype," 72(12) Journal of Virology 10260-64 (1998).
George., "Gene therapy progress and prospects: adenoviral vectors," Gene Therapy (2003) 10, 1135-1141.
Gorecki, "Prospects and problems of gene therapy: an update," (2001) Expert Opin. Emerging Drugs 6(2): 187-98.
Greber et al., "Stepwise Dismantling of Adenovirus 2 during Entry into Cells," Cell, 75, 477-486 (1993). Abstract.
Green et al., "Evidence for a repeating cross, sheet structure in the adenovirus fibre," EMBO Journal, 2(8), 1357-1365 (1983).
Grubb et al., Inefficient gene transfer by adenovirus vector to cystic fibrosis airway epithelia of mice and humans, Nature, 371, 802-806 (1994). Abstract.
Gurunathan et al., American Association of Immunologists, "CD40 Ligand/Trimer DNA Enhances Both Humoral and Cellular Immune Responses and Induces Protective Immunity to Infectious and Tumor Challenge," 1998, pp. 4563-4571, vol. 161. Abstract.
Han et al., "Ligand-directed retroviral targeting of human breast cancer cells," Proc. Natl. Acad. Sci. USA, 92, 9747-9751 (1995).
He et al., "A simplified system for generating recombinant adenoviruses," Proc. Natl. Acad. Sci. USA vol. 95, pp. 2509-2514, Mar. 1998.
Henry et al., "Characterization of the Knob Domain of the Adenovirus Type 5 Fiber Protein Expressed in *Escherichia coli*," Journal of Virology, 68(8), 5239-5246 (1994).
Hidaka, et al., "CAR-dependent and CAR-independent pathways of adenovirus vector-mediated gene transfer and expression in human fibroblasts," 103(4) The Journal of Clinical Investigation 579-87 (Feb. 1999).
Hierholzer et al., "Adenoviruses from Patients with AIDS: A Plethora of Serotypes and a Description of Five New Serotypes of Subgenus D (Types 43-47)," The Journal of Infectious Diseases vol. 158, No. 4 Oct. 1988.
Hong et al., "The Amino Terminus of the Adenovirus Fiber Protein Encodes the Nuclear Localization Signal," Virology, 185(2), 758-767 (1991). Abstract.
Horvath et al., "Nonpermissivity of Human Peripheral Blood Lymphocytes to Adenovirus Type 2 Infection," Journal of Virology, 62(1), 341-345 (1988).
Huang et al., "Upregulation of Integrins $\gamma3$ and $\gamma5$ on Human Monocytes and T Lymphocytes Facilitates Adenovirus-Mediated Gene Delivery," Journal of Virology, 69(4), 2257-2263 (1995).
Imler et al., "Novel complementation cell lines derived from human lung carcinoma A549 cells support the growth of E1-deleted adenovirus vectors," Gene Therapy, vol. 3: p. 75-84, 1996.
Jolly, Viral vector systems for gene therapy, 1994, Cancer Gene Therapy, pp. 51-64, vol. 1, No. 1.
Kang et al., "Molecular Cloning and Physical Mapping of the DNA of Human Adenovirus Type 35," Acta Microbiologica Hungarica 36 (1), pp. 67-75 (1989).
Kang et al., "Relationship of E1 and E3 Regions of Human Adenovirus 35 to Those of Human Adenovirus Subgroups A, C and D," Acta Microbiologica Hungarica 36 (4), pp. 445-457 (1989).
Karayan et al., "Oligomerization of Recombinant Penton Base of Adenovirus Type 2 and Its Assembly with Fiber in Baculovirus-Infected Cells," Virology, 202, 782-795 (1994).
Kass-Eisler et al., "Quantitative determination of adenovirus-mediated gene delivery to rat cardiac myocytes in vitro and in vivo," Proc. Natl. Acad. Sci. USA, 90, 11498-11502 (1993).
Kmiec, "Gene Therapy," American Scientist, vol. 87, pp. 240.
Komoriya et al., The Minimal Essential Seqūence for a Major Cell Type-specific Adhesion Site (CS1) within the Alternatively Spliced Type III Connecting Segment Domain of Fibronectin is Leucine-Aspartic Acid-Valine,: Journal of Biological Chemistry, 266(23), 15075-15079 (1991).

Krasnykh et al.: "Generation of Recombinant Adenovirus Vectors With Modified Fibers for Altering Viral Tropism" Journal of Virology, The American Society for Microbiology, US, vol. 70, No. 10, Oct. 1, 1996, pp. 6839-6846, XP002067518 ISSN: 0022-538X.

Lattanzi, et al., "High Efficiency Myogenic Conversion of Human Fibroblasts by Adenoviral Vector-mediated MyoD Gene Transfer," 101(10) J. Clin. Invest. 2119-28 (May 1998).

Lee et al., "The constitutive expression of the immunomodulatory gp 19k protein in E1-, E3- adenoviral vectors strongly reduces the host cytotoxic T cell response against the vector," Gene Therapy (1995) 2, 256-262.

Levrero et al., "Defective and nondefective adenovirus vectors for expressing foreign genes in vitro and in vivo," Gene, 101 (1991) 195-202.

Li et al., "Genetic Relationship between Thirteen Genome Types of Adenovirus 11, 34, and 35 with Different Tropisms," Intervirology 1991;32:338-350.

Liu et al., Molecular Basis of the inflammatory response to adenovirus vectors. Gene Therapy Oct. 2003, 935-40.

Maraveyas et al., "Targeted Immunotherapy B an update with special emphasis on ovarian cancer," Acta Oncologica, 32(7/8), 741-746 (1993). Abstract.

Mastrangeli et al., "'Sero-Switch' Adenovirus-Mediated in Vivo Gene Transfer: Circumvention of Anti-Adenovirus Humoral Immune Defenses Against Repeat Adenovirus Vector Administration by Changing the Adenovirus Serotype," Human Gene Therapy, 7, 79-87 (1996). Abstract.

Mathias et al., "Multiple Adenovirus Serotypes Use alpha-v Integrins for Infection," Journal of Virology, 68(10), 6811-6814 (1994).

Mautner et al., "Recombination in Adenovirus: Analysis of Crossover Sites in Intertypic Overlap Recombinants," Virology, 139, 43-52, (1984).

Mautner et al., "Recombination in Adenovirus: DNA Sequence Analysis of Crossover Sites in Intertypic Recombinants," Virology, 131, 1-10(1983).

Merriam-Webster Dictionary (on line) retrieved from the internet<URL:htpp://www. m-w.com/cgi-bin/dictionary, "derive," 2002.

Michael et al., "Addition of a short peptide ligand to the adenovirus fiber protein," Gene Therapy, 2, 660-668 (1995).

Michael et al., "Binding-incompetent Adenovirus Facilitates Molecular Conjugate-mediated Gene Transfer by the Receptor-mediated Endocytosis Pathway," Journal of Biological Chemistry, 268(10), 6866-6869 (1993).

Miller et al., "Targeted vectors for gene therapy," FASEB Journal, 9, 190-199 (1995).

Neda et al., "Chemical Modification of an Ecotropic Murine Leukemia Virus Results in Redirection of its Target Cell Specificity," Journal of Biological Chemistry, 266(22), 14143-14146 (1991).

Nemerow et al., "Adenovirus entry into host cells: a role for alpha-v integrins," Trends in Cell Biology, 4, 52-55 (1994).

Nemerow et al., "The Role of alpha-v Integrins in Adenovirus Infection," Biology of Vitronectins and their Receptors, 177-184 (1993).

Ngo et al., The Protein Folding Problem and Tertiary Structure Prediction, "Computational Complexity, Protein Structure Prediction, and the Levinthal Paradox," 1994, Merz et al. (editors), Birkhauser, Boston, MA, pp. 433 and 492-495.

Novelli et al., "Deletion Analysis of Functional Domains in Baculovirus-Expressed Adenovirus Type 2 Fiber," Virology, 185, 365-376 (1991).

Orkin et al., "Report and Recommendations of the Panel to Assess the NIH Investment in Research on Gene Therapy," (1995), [Retrieved on Nov. 16, 2004] [online] Retrieved from http://www.nih.gov/news/panelrep.html.

Peteranderl et al., "Trimerization of the Heat Shock Transcription Factor by a Triple-Stranded -Helical Coiled-Coil," Biochemistry, 31, 12272-12276 (1992). Abstract.

Prince, "Gene Transfer: A Review of Methods and Applications," Pathology (1998), 30, pp. 335-347.

Pring-Åkerblom et al., "Sequence Characterization and Comparison of Human Adenovirus Subgenus B and E Hexons," Virology, 212, 232-36 (1995).

Ragot et al.,: "Efficient adenovirus-mediated transfer of a human minidystrophin gene to skeletal muscle of mdx mice" Nature, Macmillan Journals Ltd. London, GB, vol. 361, No. 6413, 1993, pp. 647-650, XP002162515 ISSN: 0028-0836. Abstract.

Rea et al., "Highly efficient transduction of human monocyte-derived dendritic cells with subgroup B fiber-modified adenovirus vectors enhances transgene-encoded antigen presentation to cytotoxic T cells." Journal of Immunology, (Apr. 15, 2000) 166 (8) 5236-44. ,—Apr. 15, 2001 XP002192775.

Robbins et al., "Viral Vectors for Gene Therapy," Pharmacol. Ther. vol. 80, No. 1, pp. 35-47, 1998.

Roberts et al., "Three-Dimensional Structure of the Adenovirus Major Coat Protein Hexon," Science, 232, 1148-51 (1986).

Roelvink et al., The Coxsackievirus-Adenovirus Receptor Protein Can Function as a Cellular Attachment Protein for Adenovirus Serotypes from Subgroups A, C, D, E, and F, Journal of Virology, Oct. 1998, p. 7909-7915, vol. 72, No. 10.

Romano, "Gene Transfer in Experimental Medicine," Drug & News Perspectives, vol. 16, No. 5, 2003, 13 pages.

Russell et al., "Retroviral vectors displaying functional antibody fragments," Nucleic Acids Research, 21(5), 1081-1085 (1993).

Russell, "Replicating Vectors for Gene Therapy of Cancer: Risks, Limitations and Prospects," European Journal of Cancer, vol. 30A, No. 8, pp. 1165, 1994.

Sabourin et al., "The molecular regulation of myogenesis," (2000) Clin. Genet. 57(1): 16-25.

Schnurr et al., "Two New Candidate Adenovirus Serotypes," Intervirology 1993;36:79-83.

Schulick et al., "Established Immunity Precludes Adenovirus-mediated Gene Transfer in Rat Carotid Arteries," The Journal of Clinical Investigation vol. 99, No. 2, Jan. 1997, 209-219.

Segerman et al.: "Adenovirus types 11p and 35p show high binding efficiencies for committed hematopoietic cell lines and are infective to these cell lines" Journal of Virology, The American Society for Microbiology, US, vol. 74, No. 3, Feb. 2000, pp. 1457-1467, XP002161682 ISSN: 0022-538X.

Shayakhmetov et al., "Efficient Gene Transfer into Human CD34+ Cells by a Retargeted Adenovirus Vector," Journal of Virology, Mar. 2000, p. 2567-2583.

Signäs et al., "Adenovirus 3 Fiber Polypeptide Gene: Implications for the Structure of the Fiber Protein," Journal of Virology, 53(2), 672-678 (1985).

Silver et al., "Interaction of Human Adenovirus Serotype 2 with Human Lymphoid Cells," Virology, 165, 377-387 (1988).

Stevenson et al., Selective Targeting of Human Cells by a Chimeric Adenovirus Vector Containing a Modified Fiber Protein, 1997, Journal of Virology, pp. 4782-4790, vol. 71.

Stewart et al., "Difference imaging of adenovirus: bridging the resolution gap between X-ray crystallography and electron microscopy," EMBO Journal, 12(7), 2589-2599 (1993).

Stratford-Perricaudet LD et al.: "Widespread Long-Term Gene Transfer to Mouse Skeletal Muscles and Heart" Journal of Clinical Investigation, New York, NY, US, vol. 90 No. 2, Aug. 1992, ISSN: 0021-9738.

Toogood et al., "The Adenovirus Type 40 Hexon: Sequence, Predicated Structure and Relationship to Other Adenovirus Hexons," J. gen. Virol (1989), 70, 3203-3214.

Valderrama-Leon et al., "Restriction Endonuclease Mapping of Adenovirus 35, a Type Isolated from Immunocompromised Hosts," Journal of Virology, Nov. 1985, p. 647-650.

Verma et al., Nature, "Gene therapy-promises, problems and prospects," Sep. 1997, vol. 389, pp. 239-242.

Wadell, "Molecular Epidemiology of Human Adenoviruses," Microbiology and Immunology, vol. 110 pp. 191-220.

Wagner et al., "Coupling of adenovirus to transferrin-polylysine/DNA complexes greatly enhances receptor-mediated gene delivery and expression of transfected genes," Proc. Natl. Acad. Sci. USA, 89, 6099-6103 (1992).

Watson et al., "An Antigenic Analysis of the Adenovirus Type 2 Fibre Polypeptide," Journal of Virology, 69, 525-535 (1988).

Wickham et al., "Integrin αγβ5 Selectively Promotes Adenovirus Mediated Cell Membrane Permeabilization," Journal of Cell Biology, 127(1), 257-264 (1994).

Wickham et al., "Integrins $α_vβ_3$ and $α_vβ_5$ Promote Adenovirus Internalization but Not Virus Attachment," Cell, 73, 309-319 (1993).

Wickham et al.: "Increased in Vitro and in Vivo Gene Transfer by Adenovirus Vectors Containing Chimeric Fiber Proteins," Journal of Virology, Nov. 1997, p. 8221-8229.

Zhong et al.: "Recombinant Advenovirus is an Efficient and Non-Pertubing Genetic Vector for Human Dendritic Cells" European Journal of Immunology, Weinheim, DE, vol. 29, No. 3, 1999, pp. 964-972, XP000938797 ISSN: 0014-2980. Abstract.

PCT International Search Report, PCT/EP03/50125, dated Sep. 19, 2003.

PCT International Preliminary Examination Report, PCT/EP03/50125, dated Jun. 18, 2004.

Flomenberg et al., "Sequence and genetic Organization of Adenovirus Type 35 Early Region 3," Journal of Virology, Nov. 1988, pp. 4431-4437, vol. 62, No. 11.

Gahery-Segard et al., "Immune response to recombinant Capsid Proteins of Adenovirus in Humans: Antifiber and Anti-Penton Base Antibodies Have a Synergistic Effect on Neutralizing Activity," Journal of Virology, Mar. 1998, pp. 2388-2397, vol. 72, No. 3.

Notice of Opposition to a European Patent, Patent No. 1054064, by Cell Genesys Inc., dated Jul. 5, 2005.

Rosenfeld et al., Adenovirus-Mediated Transfer of a recombinant alpha-1-Antitrypsin Gene to the Lung Epithelium in Vivo, Science, Apr. 19, 1991, pp. 431-434, vol. 252.

Roy et al., "Circumvention of Immunity to the Adenovirus major Coat Protein Hexon," Journal of Virology, Aug. 1998, pp. 6875-6879, vol. 72, No. 8.

Stevenson et al., "Human Adenovirus Serotypes 3 and 5 Bind to Two Different Cellular receptors via the Fiber Head Domain," Journal of Virology, May 1995, pp. 2850-2857, vol. 69, No. 5.

Stratford-Perricaudet et al., "Evaluation of the Transfer and Expression in Mice of an Enzyme-Encoding Gene Using a Human Adenovirus Vector," Human Gene Therapy, 1990, pp. 241-256, vol. 1.

Hehir et al., Molecular Characterized of Replication-Competent Variants of Adenovirus Vectors and Genome Modifications to Prevent Their Occurrence, J. Virol. 70:8459-8467(1996).

Nan et al., Development of an Ad7 cosmid system and generation of an Ad7DE1DE3HIVMN env/rev recombinant virus, Gene Therapy, 2003, pp. 326-336, vol. 10.

Reddy et al., Development of adenovirus serotype 35 as a gene transfer vector, Virology, 2003, pp. 384-393, vol. 311.

Vogels et al., Replication-Deficient Human Adenovirus Type 35 Vectors for Gene Transfer and Vaccination: efficient Human Cell Infection and ByPass of Preexisting Adenovirus Immunity, J. Virology, 2003, pp. 8263-8671, vol. 77, No. 15.

Xu et al., Approaches to improving the kinetics of adenovirus-delivered genes and gene products, Advanced Drug Delivery Reviews, 2005, pp. 781-802, vol. 57.

Crawford-Miksza et al., Adenovirus Serotype Evolution is Driven by Illegitimate Recombination in the Hypervariable Regions of the Hexon Protein, Virology, 1996, pp. 357-367, vol. 224.

Crawford-Miksza et al., Strain Variation in Adenovirus Serotypes 4 and 7a Causing Acute Respiratory Disease, Journal of Clinical Microbiology, Apr. 1999, pp. 1107-1112, vol. 37, No. 4.

Parker et al., Effect of Neutralizing Sera on Factor X-Mediated Adenovirus Serotype 5 Gene Transfer, Journal of Virology, Jan. 2009, pp. 479-483, vol. 83, No. 1.

Schmitz et al., Worldwide Epidemiology of Human Adenovirus Infections, American Journal of Epidemiology, 1982, pp. 455-466, vol. 117, No. 4.

Thomas et al., Progress and Problems with the Use of Viral Vectors for Gene Therapy, Nature Publishing Group, May 2003, pp. 346-358, vol. 4.

Verma et al., Gene therapy—promises, problems and prospects, Nature, Sep. 18, 1997, pp. 239-242, vol. 389.

* cited by examiner

```
  1  M T T S G V P F G M T L R P T R S R L S R R T P Y S R D R L P P F F E T - - E T R A T I L E D H P L L P  Ad5.E4-ORF6.PRO
  1  M T T S G V P F G M T L R P T R S R L S R R T P Y S R D R L P P F F E T - - E T R A T I L E D H P L L P  Orf6 aaseq in Ad35.PR.50rf6.PRO
  1  M S G S N S I M T R - L R A R S T S C A R H H P Y T R A Q L P R C E E N E T R A S M T E D H P L L P      Ad35.E4-ORF6.PRO 50  E C N T L T M H N V S Y V R G L P C S V G F T L I Q E W V V P W D M V L T R E E L V I L R K C M H V      Ad5.E4-ORF6.PRO
 50  E C N T L T M H N V S Y V R G L P C S V G F T L I Q E W V V P W D M V L T R E E L V I L R K C M H V      Orf6 aaseq in Ad35.PR.50rf6.PRO
 50  D C D T M T M H S S C V R G L P C S A S F T V L Q E L P I P W D M F L N P E E L K I M R R C M H L       Ad35.E4-ORF6.PRO 100  C L C C A N I D I M T S M M I H G Y E S N A L H C H C S S P G S L Q C I A G G Q V L A S W F R M V V      Ad5.E4-ORF6.PRO
100  C L C C A N I D I M T S M M I H G Y E S N A L H C H C S S P G S L Q C I A G G Q V L A S W F R M V V      Orf6 aaseq in Ad35.PR.50rf6.PRO
100  C L C C A T I D I F H S Q V I H G R E N W L H C H C N Q Q G S L Q C M A G G A V L A V W F R K V I       Ad35.E4-ORF6.PRO 150  D G A M F N Q R E I W Y R E V V N Y N M P K E V M F M S S V F M R G R H L I Y L R L W Y D G H V G S      Ad5.E4-ORF6.PRO
150  D G A M F N Q R E I W Y R E V V N Y N M P K E V M F M S S V F M R G R H L I Y L R L W Y D G H V G S      Orf6 aaseq in Ad35.PR.50rf6.PRO
150  L G C M I N Q R C P W Y R Q I V N M H M P K E I M Y V G S V F L R E R H L I Y I K L W Y D G H A G A      Ad35.E4-ORF6.PRO 200  V V P A M S F G Y S A L H C G I L N N I V V L C C S Y C A D L S E I R V R C C A R R T R R L M L R A      Ad5.E4-ORF6.PRO
200  V V P A M S F G Y S A L H C G I L N N I V V L C C S Y C A D L S E I R V R C C A R R T R R L M L R A      Orf6 aaseq in Ad35.PR.50rf6.PRO
200  I I S D M S F G W S A F N Y G L L N N I V I M C C T Y C K D L S E I R M R C C A H R T R K L M L R A      Ad35.E4-ORF6.PRO 250  V R I I A E E T T A - - M L Y S C R T E R R Q Q F I R A L L Q H H R P I L M H D Y D S - - - T P M        Ad5.E4-ORF6.PRO
250  V R I I A E E T T A - - M L Y S C R T E R R Q Q F I R A L L Q H H R P I L M H D Y D S - - - T P M        Orf6 aaseq in Ad35.PR.50rf6.PRO
250  I K I M L Q E T V D P D P I N S S R T E R R R Q R L L V G L M R H N R P I P F S D Y D S H R S S S R     Ad35.E4-ORF6.PRO Decoration 'Decoration #1': Box residues that differ from Ad5.E4-ORF6.PRO.
```

FIG. 11

```
  1  M T T S G V P F G M T L R P T R S R L S R R T P Y S R D R L P P F E E T - E T R A    Ad5.E4-ORF6+7.PRO
  1  M T T S G V P F G M T L R P T R S R L S R R T P Y S R D R L P P F E E T - E T R A    Orf6+7 aaseq in Ad35.PR5Orf6.PRC
  1  M S G S N - S I M T R L R A R S T S C A R H H P Y T R A Q L P R C E E N E T R A    Ad35.E4-ORF6+7.pro 40  T I L E D H P L L P E C N T L T M H N A W T S P S P P V K Q P Q P V G Q Q P V A Q    Ad5.E4-ORF6+7.PRO
 40  T I L E D H P L L P E C N T L T M H N A W T S P S P P V K Q P Q P V G Q Q P V A Q    Orf6+7 aaseq in Ad35.PR5Orf6.PRC
 40  S M T E D H P L L P D C D T M T M H S M T V I Q T P - - - - - E S H P Q    Ad35.E4-ORF6+7.pro 80  Q L D S D M N L S E L P G E F I N I T D E R L A R Q E T V W N I T P K N M S V T    Ad5.E4-ORF6+7.PRO
 80  Q L D S D M N L S E L P G E F I N I T D E R L A R Q E T V W N I T P K N M S V T    Orf6+7 aaseq in Ad35.PR5Orf6.PRC
 71  Q L D C E S A L K D Y R D G F L S I T D P R L A R S E T V W N V E S K T M S I S    Ad35.E4-ORF6+7.pro 120  H D M M L F K A S R G E R T V Y S V C W E G G G R L N T R V L    Ad5.E4-ORF6+7.PRO
120  H D M M L F K A S R G E R T V Y S V K W E G G G K I T T R I L    Orf6+7 aaseq in Ad35.PR5Orf6.PRC
111  N G I Q M F K A V R G E R L V Y S V K W E G G G K I T T R I L    Ad35.E4-ORF6+7.pro
```

Decoration 'Decoration #1': Box residues that differ from Ad5.E4-ORF6+7.PRO.

FIG. 12

```
SEQUENCE LISTING

<160> NUMBER OF SEQ ID NOS: 25

<210> SEQ ID NO 1
<211> LENGTH: 31
<212> TYPE: DNA
<213> ORGANISM: Artificial Sequence
<220> FEATURE:
<223> OTHER INFORMATION: primer 35FR

<400> SEQUENCE: 1
cgggatccac tttattttag ttgtcgtctt c                              31

<210> SEQ ID NO 2
<211> LENGTH: 37
<212> TYPE: DNA
<213> ORGANISM: Artificial Sequence
<220> FEATURE:
```

```
<223> OTHER INFORMATION: primer 35R4

<400> SEQUENCE: 2
cggaattctt aattaaggga aatgcaaatc tgtgagg                              37

<210> SEQ ID NO 3
<211> LENGTH: 20
<212> TYPE: DNA
<213> ORGANISM: Artificial Sequence
<220> FEATURE:
<223> OTHER INFORMATION: primer 35psi-For

<400> SEQUENCE: 3
gtggtattta tggcagggtg                                                20

<210> SEQ ID NO 4
<211> LENGTH: 20
<212> TYPE: DNA
<213> ORGANISM: Artificial Sequence
<220> FEATURE:
<223> OTHER INFORMATION: primer DF35-1

<400> SEQUENCE: 4
cactcaccac ctccaattcc                                                20

<210> SEQ ID NO 5
<211> LENGTH: 30
<212> TYPE: DNA
<213> ORGANISM: Artificial Sequence
<220> FEATURE:
<223> OTHER INFORMATION: primer 5E4F

<400> SEQUENCE: 5
cgggatccgt ttgtgttatg tttcaacgtg                                     30

<210> SEQ ID NO 6
<211> LENGTH: 32
<212> TYPE: DNA
<213> ORGANISM: Artificial Sequence
<220> FEATURE:
<223> OTHER INFORMATION: primer 5E4R

<400> SEQUENCE: 6
gctggcgagc tcggcggagt aacttgtatg tg                                  32

<210> SEQ ID NO 7
<211> LENGTH: 31
<212> TYPE: DNA
<213> ORGANISM: Artificial Sequence
<220> FEATURE:
<223> OTHER INFORMATION: primer 35SITR

<400> SEQUENCE: 7
gatccggagc tcacaacgtc attttcccac g                                   31

<210> SEQ ID NO 8
<211> LENGTH: 25
<212> TYPE: DNA
<213> ORGANISM: Artificial Sequence
<220> FEATURE:
<223> OTHER INFORMATION: primer 3S3ITR

<400> SEQUENCE: 8
aggaattcgc ggccgcattt aaatc                                          25
```

```
<210> SEQ ID NO 9
<211> LENGTH: 18
<212> TYPE: DNA
<213> ORGANISM: Artificial Sequence
<220> FEATURE:
<223> OTHER INFORMATION: primer E4-F1

<400> SEQUENCE: 9
agaggaacac attccccc                                                   18

<210> SEQ ID NO 10
<211> LENGTH: 32
<212> TYPE: DNA
<213> ORGANISM: Artificial Sequence
<220> FEATURE:
<223> OTHER INFORMATION: primer E4-R2

<400> SEQUENCE: 10
ggggagaaag gactgtgtat tctgtcaaat gg                                   32

<210> SEQ ID NO 11
<211> LENGTH: 35
<212> TYPE: DNA
<213> ORGANISM: Artificial Sequence
<220> FEATURE:
<223> OTHER INFORMATION: primer E4-F3

<400> SEQUENCE: 11
tttgacagaa tacacagtcc tttctccccg gctgg                                35

<210> SEQ ID NO 12
<211> LENGTH: 33
<212> TYPE: DNA
<213> ORGANISM: Artificial Sequence
<220> FEATURE:
<223> OTHER INFORMATION: primer E4-R4

<400> SEQUENCE: 12
acaaaatacg agaatgacta cgtccggcgt tcc                                  33

<210> SEQ ID NO 13
<211> LENGTH: 30
<212> TYPE: DNA
<213> ORGANISM: Artificial Sequence
<220> FEATURE:
<223> OTHER INFORMATION: primer E4-F5

<400> SEQUENCE: 13
ggacgtagtc attctcgtat tttgtatagc                                      30

<210> SEQ ID NO 14
<211> LENGTH: 18
<212> TYPE: DNA
<213> ORGANISM: Artificial Sequence
<220> FEATURE:
<223> OTHER INFORMATION: primer E4-R6

<400> SEQUENCE: 14
tcaccaacac agtggggg                                                   18

<210> SEQ ID NO 15
<211> LENGTH: 20
<212> TYPE: DNA
<213> ORGANISM: Artificial Sequence
<220> FEATURE:
<223> OTHER INFORMATION: primer NF-1
```

-continued

<400> SEQUENCE: 15
ccacaacccc cactactccc                                                    20

<210> SEQ ID NO 16
<211> LENGTH: 21
<212> TYPE: DNA
<213> ORGANISM: Artificial Sequence
<220> FEATURE:
<223> OTHER INFORMATION: primer NR-2

<400> SEQUENCE: 16
cgtctcttcc ctctcctctc c                                                  21

<210> SEQ ID NO 17
<211> LENGTH: 20
<212> TYPE: DNA
<213> ORGANISM: Artificial Sequence
<220> FEATURE:
<223> OTHER INFORMATION: primer NcoI-R

<400> SEQUENCE: 17
aggatcatcc gctgctgccc                                                    20

<210> SEQ ID NO 18
<211> LENGTH: 19
<212> TYPE: DNA
<213> ORGANISM: Artificial Sequence
<220> FEATURE:
<223> OTHER INFORMATION: primer NcoI-F

<400> SEQUENCE: 18
catcaggata gggcggtgg                                                     19

<210> SEQ ID NO 19
<211> LENGTH: 20
<212> TYPE: DNA
<213> ORGANISM: Artificial Sequence
<220> FEATURE:
<223> OTHER INFORMATION: primer 35E3for

<400> SEQUENCE: 19
aatgactaat gcaggtgcgc                                                    20

<210> SEQ ID NO 20
<211> LENGTH: 28
<212> TYPE: DNA
<213> ORGANISM: Artificial Sequence
<220> FEATURE:
<223> OTHER INFORMATION: primer 35E3rev

<400> SEQUENCE: 20
cgacgcgttg tagtcgttga gcttctag                                           28

<210> SEQ ID NO 21
<211> LENGTH: 294
<212> TYPE: PRT
<213> ORGANISM: Artificial Sequence
<220> FEATURE:
<223> OTHER INFORMATION: Amino acid sequence of the E4-orf6 protein of
      Adenovirus type 5

<400> SEQUENCE: 21

Met Thr Thr Ser Gly Val Pro Phe Gly Met Thr Leu Arg Pro Thr Arg
1               5                   10                  15

Ser Arg Leu Ser Arg Arg Thr Pro Tyr Ser Arg Asp Arg Leu Pro Pro

```
                20                  25                  30
Phe Glu Thr Glu Thr Arg Ala Thr Ile Leu Glu Asp His Pro Leu Leu
            35                  40                  45

Pro Glu Cys Asn Thr Leu Thr Met His Asn Val Ser Tyr Val Arg Gly
 50                  55                  60

Leu Pro Cys Ser Val Gly Phe Thr Leu Ile Gln Glu Trp Val Val Pro
65                  70                  75                  80

Trp Asp Met Val Leu Thr Arg Glu Glu Leu Val Ile Leu Arg Lys Cys
                85                  90                  95

Met His Val Cys Leu Cys Cys Ala Asn Ile Asp Ile Met Thr Ser Met
            100                 105                 110

Met Ile His Gly Tyr Glu Ser Trp Ala Leu His Cys His Cys Ser Ser
        115                 120                 125

Pro Gly Ser Leu Gln Cys Ile Ala Gly Gly Gln Val Leu Ala Ser Trp
    130                 135                 140

Phe Arg Met Val Val Asp Gly Ala Met Phe Asn Gln Arg Phe Ile Trp
145                 150                 155                 160

Tyr Arg Glu Val Val Asn Tyr Asn Met Pro Lys Glu Val Met Phe Met
                165                 170                 175

Ser Ser Val Phe Met Arg Gly Arg His Leu Ile Tyr Leu Arg Leu Trp
            180                 185                 190

Tyr Asp Gly His Val Gly Ser Val Val Pro Ala Met Ser Phe Gly Tyr
        195                 200                 205

Ser Ala Leu His Cys Gly Ile Leu Asn Asn Ile Val Val Leu Cys Cys
    210                 215                 220

Ser Tyr Cys Ala Asp Leu Ser Glu Ile Arg Val Arg Cys Cys Ala Arg
225                 230                 235                 240

Arg Thr Arg Arg Leu Met Leu Arg Ala Val Arg Ile Ile Ala Glu Glu
                245                 250                 255

Thr Thr Ala Met Leu Tyr Ser Cys Arg Thr Glu Arg Arg Gln Gln
            260                 265                 270

Phe Ile Arg Ala Leu Leu Gln His His Arg Pro Ile Leu Met His Asp
        275                 280                 285

Tyr Asp Ser Thr Pro Met
    290

<210> SEQ ID NO 22
<211> LENGTH: 299
<212> TYPE: PRT
<213> ORGANISM: Artificial Sequence
<220> FEATURE:
<223> OTHER INFORMATION: Amino acid sequence of the E4-orf6 protein of
      Adenovirus type 35

<400> SEQUENCE: 22

Met Ser Gly Ser Asn Ser Ile Met Thr Arg Leu Arg Ala Arg Ser Thr
1               5                   10                  15

Ser Cys Ala Arg His His Pro Tyr Thr Arg Ala Gln Leu Pro Arg Cys
            20                  25                  30

Glu Glu Asn Glu Thr Arg Ala Ser Met Thr Glu Asp His Pro Leu Leu
        35                  40                  45

Pro Asp Cys Asp Thr Met Thr Met His Ser Val Ser Cys Val Arg Gly
    50                  55                  60

Leu Pro Cys Ser Ala Ser Phe Thr Val Leu Gln Glu Leu Pro Ile Pro
65                  70                  75                  80
```

-continued

```
Trp Asp Met Phe Leu Asn Pro Glu Glu Leu Lys Ile Met Arg Arg Cys
                 85                  90                  95

Met His Leu Cys Leu Cys Cys Ala Thr Ile Asp Ile Phe His Ser Gln
            100                 105                 110

Val Ile His Gly Arg Glu Asn Trp Val Leu His Cys His Cys Asn Gln
        115                 120                 125

Gln Gly Ser Leu Gln Cys Met Ala Gly Gly Ala Val Leu Ala Val Trp
    130                 135                 140

Phe Arg Lys Val Ile Leu Gly Cys Met Ile Asn Gln Arg Cys Pro Trp
145                 150                 155                 160

Tyr Arg Gln Ile Val Asn Met His Met Pro Lys Glu Ile Met Tyr Val
                165                 170                 175

Gly Ser Val Phe Leu Arg Arg His Leu Ile Tyr Ile Lys Leu Trp
            180                 185                 190

Tyr Asp Gly His Ala Gly Ala Ile Ile Ser Asp Met Ser Phe Gly Trp
        195                 200                 205

Ser Ala Phe Asn Tyr Gly Leu Leu Asn Asn Ile Val Ile Met Cys Cys
    210                 215                 220

Thr Tyr Cys Lys Asp Leu Ser Glu Ile Arg Met Arg Cys Cys Ala His
225                 230                 235                 240

Arg Thr Arg Lys Leu Met Leu Arg Ala Ile Lys Ile Met Leu Gln Glu
                245                 250                 255

Thr Val Asp Pro Asp Pro Ile Asn Ser Ser Arg Thr Glu Arg Arg Arg
            260                 265                 270

Gln Arg Leu Leu Val Gly Leu Met Arg His Asn Arg Pro Ile Pro Phe
        275                 280                 285

Ser Asp Tyr Asp Ser His Arg Ser Ser Ser Arg
    290                 295

<210> SEQ ID NO 23
<211> LENGTH: 150
<212> TYPE: PRT
<213> ORGANISM: Artificial Sequence
<220> FEATURE:
<223> OTHER INFORMATION: Amino acid sequence of the E4-orf6+7 protein
      of Adenovirus type 5

<400> SEQUENCE: 23

Met Thr Thr Ser Gly Val Pro Phe Gly Met Thr Leu Arg Pro Thr Arg
1               5                   10                  15

Ser Arg Leu Ser Arg Arg Thr Pro Tyr Ser Arg Asp Arg Leu Pro Pro
            20                  25                  30

Phe Glu Thr Glu Thr Arg Ala Thr Ile Leu Glu Asp His Pro Leu Leu
        35                  40                  45

Pro Glu Cys Asn Thr Leu Thr Met His Asn Ala Trp Thr Ser Pro Ser
    50                  55                  60

Pro Pro Val Lys Gln Pro Gln Val Gly Gln Gln Pro Val Ala Gln Gln
65                  70                  75                  80

Leu Asp Ser Asp Met Asn Leu Ser Glu Leu Pro Gly Glu Phe Ile Asn
                85                  90                  95

Ile Thr Asp Glu Arg Leu Ala Arg Gln Glu Thr Val Trp Asn Ile Thr
            100                 105                 110

Pro Lys Asn Met Ser Val Thr His Asp Met Met Leu Phe Lys Ala Ser
        115                 120                 125

Arg Gly Glu Arg Thr Val Tyr Ser Val Cys Trp Glu Gly Gly Gly Arg
    130                 135                 140
```

```
Leu Asn Thr Arg Val Leu
145                 150

<210> SEQ ID NO 24
<211> LENGTH: 150
<212> TYPE: PRT
<213> ORGANISM: Artificial Sequence
<220> FEATURE:
<223> OTHER INFORMATION: Amino acid sequence of the E4-orf6+7 fusion
      protein from Adenovirus type 5 and Adenovirus type 35

<400> SEQUENCE: 24

Met Thr Thr Ser Gly Val Pro Phe Gly Met Thr Leu Arg Pro Thr Arg
1               5                   10                  15

Ser Arg Leu Ser Arg Arg Thr Pro Tyr Ser Arg Asp Arg Leu Pro Pro
                20                  25                  30

Phe Glu Thr Glu Thr Arg Ala Thr Ile Leu Glu Asp His Pro Leu Leu
            35                  40                  45

Pro Glu Cys Asn Thr Leu Thr Met His Asn Ala Trp Thr Ser Pro Ser
        50                  55                  60

Pro Pro Val Lys Gln Pro Gln Val Gly Gln Pro Val Ala Gln Gln
65                  70                  75                  80

Leu Asp Ser Asp Met Asn Leu Ser Glu Leu Pro Gly Glu Phe Ile Asn
                85                  90                  95

Ile Thr Asp Glu Arg Leu Ala Arg Gln Glu Thr Val Trp Asn Ile Thr
                100                 105                 110

Pro Lys Asn Met Ser Val Thr His Asp Met Met Leu Phe Lys Ala Ser
            115                 120                 125

Arg Gly Glu Arg Thr Val Tyr Ser Val Lys Trp Glu Gly Gly Lys
        130                 135                 140

Ile Thr Thr Arg Ile Leu
145                 150

<210> SEQ ID NO 25
<211> LENGTH: 141
<212> TYPE: PRT
<213> ORGANISM: Artificial Sequence
<220> FEATURE:
<223> OTHER INFORMATION: Amino acid sequence of the E4-orf6+7 protein
      of Adenovirus type 35

<400> SEQUENCE: 25

Met Ser Gly Ser Asn Ser Ile Met Thr Arg Leu Arg Ala Arg Ser Thr
1               5                   10                  15

Ser Cys Ala Arg His His Pro Tyr Thr Arg Ala Gln Leu Pro Arg Cys
                20                  25                  30

Glu Glu Asn Glu Thr Arg Ala Ser Met Thr Glu Asp His Pro Leu Leu
            35                  40                  45

Pro Asp Cys Asp Thr Met Thr Met His Ser Met Thr Val Ile Gln Thr
        50                  55                  60

Pro Glu Ser His Pro Gln Gln Leu Asp Cys Glu Ser Ala Leu Lys Asp
65                  70                  75                  80

Tyr Arg Asp Gly Phe Leu Ser Ile Thr Asp Pro Arg Leu Ala Arg Ser
                85                  90                  95

Glu Thr Val Trp Asn Val Glu Ser Lys Thr Met Ser Ile Ser Asn Gly
                100                 105                 110

Ile Gln Met Phe Lys Ala Val Arg Gly Glu Arg Leu Val Tyr Ser Val
            115                 120                 125
```

```
Lys Trp Glu Gly Gly Gly Lys Ile Thr Thr Arg Ile Leu
    130             135             140
```

MEANS AND METHODS FOR PRODUCING ADENOVIRUS VECTORS

CROSS-REFERENCE TO RELATED APPLICATIONS

This application is a divisional of application Ser. No. 10/512,589, filed Oct. 25, 2004, U.S. Pat. No. 7,468,181, which was a national phase entry under 35 U.S.C. §371 of International Patent Application PCT/EP03/50125, filed Apr. 24, 2003, published in English as International Patent Publication WO 03/104467 on Dec. 18, 2003, which claims the benefit of International Patent Application PCT/NL02/00280, filed Apr. 25, 2002, the contents of the entirety of each of which are incorporated by this reference.

TECHNICAL FIELD

The invention relates generally to biotechnology and more particularly to nucleic acid delivery vehicles and the use thereof, more in particular, the invention relates to recombinant adenoviral vectors and the use thereof.

BACKGROUND

To date, 51 human adenovirus serotypes have been identified that are subdivided into 6 subgroups (A, B, C, D, E and F) based on hemagglutination properties and sequence homology (Francki et al. 1991). The adenovirus infectious cycle is divided into an early and a late phase. In the early phase, the virus is uncoated and the genome is transported to the nucleus, after which the early gene regions (E1, E2, E3 and E4) become transcriptionally active. The E1 region contains two transcription regions: E1A and E1B. E1A encodes proteins that are involved in modification of the host cell cycle and activation of the other viral transcription regions (reviewed by Russell 2000). The E1B region encodes two major proteins, E1B-19K and E1B-55K, that prevent the induction of apoptosis resulting from the activity of the E1A proteins (Rao et al. 1992; Yew and Berk 1992; Shenk 1996). In addition, the E1B-55K protein is required in the late phase for selective viral mRNA transport and inhibition of host protein expression (Pilder et al. 1986). E2 is also divided in two subdomains, E2A and E2B, that together encode three proteins (a DNA-binding protein, a viral polymerase and a pre-terminal protein) that are all involved in replication of the viral genome (Van der Vliet 1995). E3 is not necessary for replication in vitro but encodes several proteins that subvert the host defense mechanism towards viral infection (Horwitz 2001). E4 harbors at least six open reading frames (orfs) that encode proteins involved in several distinct functions related to viral mRNA splicing and transport, host cell mRNA transport, viral and cellular transcription and transformation (reviewed by Leppard 1997). The late proteins, necessary for formation of the viral capsids and packaging of viral genomes, are all generated from the major late transcription unit (MLTU) that becomes fully active after the onset of replication. A complex process of differential splicing and polyadenylation gives rise to more than 15 mRNA species that share a tripartite leader sequence. The E1B-55K, E4-orf3 and E4-orf6 proteins play a pivotal role in the regulation of late viral mRNA processing and transport from the nucleus. For this process E1B-55K interacts with E4-orf6 to form a functional complex that stimulates transport of viral mRNAs to the cytoplasm, while the complex is also involved in inhibition of the transport of cellular mRNAs from the nucleus to the cytoplasm (reviewed in Leppard 1997 and 1998).

Production of E1-deleted vectors based on subgroup C serotypes Adenovirus serotype 5 (Ad5) or Adenovirus serotype 2 (Ad2) is achieved in E1-complementing cell lines, such as 293 (Graham et al. 1970), 911 (Fallaux et al. 1996) and PER.C6™ (Fallaux et al. 1998; ECACC deposit no. 96022940). As disclosed in WO 99/55132 and WO 01/05945, vectors and cell lines can be matched to avoid generation of replication-competent adenoviruses through homologous recombination between adenovirus sequences in the cell line and the vector. For efficient production of replication-incompetent adenoviruses derived from group C, the cell line PER.C6™ is preferably used. Using this cell line, adenovirus vectors can be matched, thereby allowing for producing group C adenoviral vectors in the absence of replication-competent adenovirus (Fallaux et al. 1998; U.S. Pat. No. 6,033,908). However, group C vectors may not always be the ideal vehicles for direct in vivo applications since the infection efficiency is seriously hampered by the presence of high titers of neutralizing activity in most humans and the absence of sufficient amounts of the cellular receptor (Coxsackie-adenovirus receptor, CAR) on specific primary target cells (e.g., endothelial cells, smooth muscle cells, synoviocytes, monocytes and dendritic cells). Administration of higher amounts of viruses to increase transduction may lead to increased toxicity and unpredictable clinical outcome due to the variation in neutralizing titers of subjects that are treated. These limitations can be overcome by the use of other serotypes of adenoviruses. For example, in the receptor-binding part of a fiber of subgroup B viruses (in particular of serotype 16), when expressed on an Ad5-based vector, Ad5-based vector-mediated infection is significantly increased in human endothelial cells and smooth muscle cells (WO 00/31285) and in human synoviocytes (WO 00/52186). The fiber of another subgroup B adenovirus, Ad35, is most efficient in mediating infection of human monocytes and dendritic cells (WO 00/03029). Furthermore, Ad35 has been identified as a virus to which the vast majority of the human population has no neutralizing activity (WO 00/70071).

There is a generally felt need in the art to develop technology that has broader serotype utility. A particular problem is the lack of suitable packaging cell lines for these other serotypes. Packaging cell lines for Ad5 vectors typically comprise E1-encoded proteins derived from adenovirus serotype 5. Examples of such "standard" packaging cell lines are 293, 911 and PER.C6™. Attempts to produce vectors derived from other serotypes on these standard packaging cell lines have proven arduous, if not unsuccessful. Occasionally, some production is seen, depending on the particular serotype used. However, yields are poor from recombinant adenovirus vectors derived from adenovirus subgroups other than subgroup C and produced on cell lines transformed and immortalized by E1 from Ad5. In a paper by Abrahamsen et al. (1997), improved plaque purification of an E1A-deleted adenovirus serotype 7 vector (subgroup B) was observed on 293 cells comprising E4-orf6 derived from adenovirus serotype 5, as compared to 293 cells lacking the E4-orf6 sequence from Ad5. However, a problem was encountered with the stability of the vector as unexpected recombinations were observed in plaque-purified stocks. An additional problem was encountered with wild-type adenovirus virus contamination during production. Moreover, for large-scale production of adenoviruses, it is not useful to co-transfect E4-orf6 to obtain titers that are high enough for application. One option for growing such adenoviruses is to provide cells with the E4-orf6 gene stably integrated into the genome of the complementing/packaging cell line. Such cells have been described in the art (e.g., WO 96/22378). A disadvantage of that system is the fact that new stable cell lines have to be generated and numerous selection rounds have to be performed before stable and proper cells have been generated. This process is laborious and time consuming. In general, it can be stated that generation and propagation of adenoviruses from serotypes other than serotype 5 (subgroup C), such as subgroup B viruses, has proven to be difficult on Ad5-complementing cells. As has been disclosed in WO 00/70071, recombinant viruses based on subgroup B virus Ad35 can be made by co-transfection of an expression construct containing the Ad35 early region-1 sequences (Ad35-E1). Furthermore, Ad35-based viruses that are deleted only for E1A sequences and not for E1B were shown to replicate efficiently on PER.C6 cells, suggesting that the E1A proteins of Ad5 are able to complement the Ad35-E1A functions (applicant's international application PCT/NL01/00824, not yet published). Moreover, the experiments show that lack of Ad35-E1B results in poor yields on Ad5-complementing cells. WO 00/70071 also discloses cell lines for producing E1-deleted non-group C adenoviral vectors by further modifying cell lines that are capable of complementing adenovirus serotype 5. WO 00/70071 further suggests that one should establish new cell lines harboring Ad35-E1 sequences for the complementation of recombinant adenovirus serotype 35 vectors lacking the E1 region (see also applicant's international application PCT/NL01/00824). However, as also discussed above, if one desires to apply a specific serotype for a specific need, one would have to establish a new cell line for every specific serotype or modify the available cell lines that can complement adenovirus serotype 5 for complementation of the serotype of interest. It would clearly be advantageous to use the established cell lines that are available in the art and not to modify these and use them for producing all other, non-Ad5 serotypes, applying the established and efficient methods known in the art. It is concluded that until the invention, no flexible and proper "production platform" was available in the art that enabled one to produce useful yields of adenovirus serotypes that were different from the serotypes of subgroup C.

SUMMARY OF THE INVENTION

Provided are recombinant adenovirus vectors comprising structural and non-structural elements of an adenovirus of a first serotype, wherein the vector further comprises a sequence encoding an E4-orf6 protein, wherein the sequence is selected from the group consisting of: a) an E4-orf6-encoding sequence derived from an adenovirus of a second serotype different from the first serotype; b) an E4-orf6-encoding sequence derived from an adenovirus of the first serotype by way of a deletion, mutation, addition and/or substitution in one or more codons; and c) an E4-orf6-encoding sequence comprising a fusion between a part of an E4-orf6-encoding sequence derived from a second serotype different from the first serotype and a part of an E4-orf6-encoding sequence derived from a third serotype, wherein the third serotype may be identical to or different from the first serotype.

Further provided are methods for producing such recombinant adenovirus vectors comprising structural and non-structural elements of an adenovirus of a first serotype, the method comprising the steps of: a) providing a complementing cell harboring an E1B-55K-encoding sequence derived from an adenovirus of a second serotype in expressible form, with the necessary elements of an adenovirus so as to allow assembly of the recombinant adenovirus vector by the complementing cell, wherein the elements comprise at least some structural and non-structural elements from an adenovirus of the first serotype different from the second serotype and a sequence encoding a functional E4-orf6 protein or a functional part, derivative and/or analogue thereof, which is compatible with the expressible E1B-55K protein in the complementing cell; b) culturing the complementing cell in a medium under conditions allowing for production and assembly of the adenovirus vector to take place; and c) harvesting the recombinant adenovirus vector so produced from the medium and/or the complementing cell, wherein the sequence encoding the compatible E4-orf6 protein is present in the recombinant adenovirus vector so produced.

Further described are pharmaceutical compositions comprising adenoviral vectors of the invention and the treatment of individuals using the adenoviral vectors provided by the invention. The invention also relates to a kit of parts comprising cell lines and adenoviral vectors provided by the invention for executing the methods provided by the invention.

BRIEF DESCRIPTION OF THE FIGURES

FIG. 11 shows the alignment between the amino acid sequence of E4-orf6 of Adenovirus serotype 5 (SEQ ID NO:21; upper sequence) with the amino acid sequence of the E4-orf6 protein from Adenovirus serotype 5 cloned into the Ad35 backbone (SEQ ID NO:21; middle sequence; NB. identical to E4-orf6 of Ad5, upper sequence) as obtained by determination of the nucleotide order, and the amino acid sequence of the E4-orf6 protein of Adenovirus serotype 35 (SEQ ID NO:22; lower sequence), showing that the entire fragment encoding the E4-orf6 protein in the Adenovirus serotype 35 backbone has been replaced by the fragment encoding the E4-orf6 protein of Adenovirus serotype 5.

FIG. 12 shows the alignment between the amino acid sequence of the E4-orf6/7 protein of Adenovirus serotype 5 (SEQ ID NO:23; upper sequence) with the amino acid sequence of the E4-orf6/7 fusion protein encoded partly by the Adenovirus serotype 5 E4-orf6/7 fragment replacing the corresponding part of the adenovirus serotype 35 E4-orf6/7 fragment in the Adenovirus serotype 35 backbone (SEQ ID NO:24; middle sequence) and the amino acid sequence of the E4-orf6/7 protein of Adenovirus serotype 35 (SEQ ID NO:25; lower sequence), showing that the orf6/7 sequence is partly chimeric, with the fusion approximately at the lysine (K) residue at position 138. For the sake of clarity, the notation orf6+7 should be read as the open reading frame orf6/7, which is a separate open reading frame within the E4 region of adenoviruses besides orf6 and orf7, being a notation well known to persons skilled in the art.

DETAILED DESCRIPTION OF THE INVENTION

Figure 1:
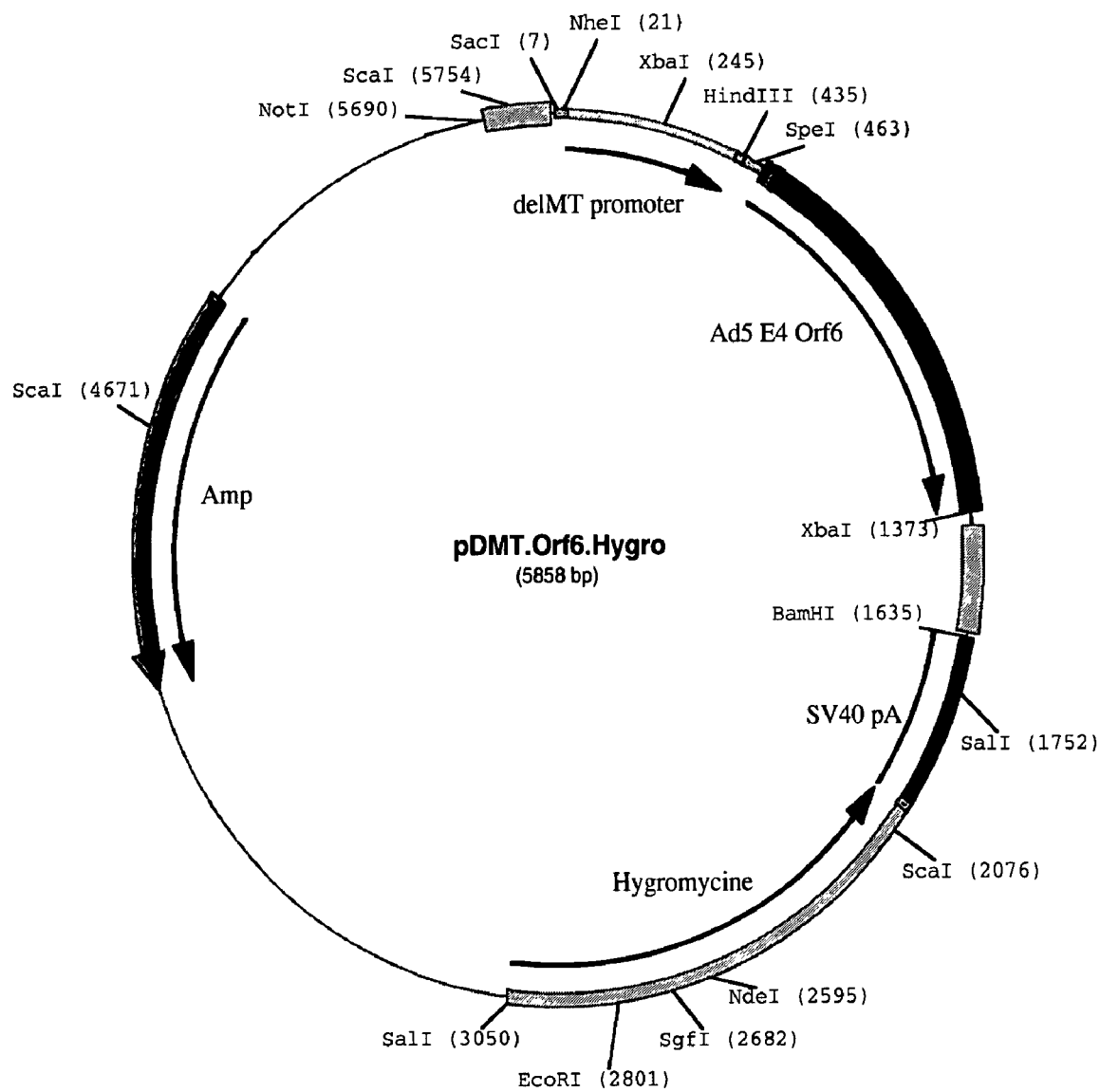
FIG. 1 is a schematic representation of plasmid pΔMT.Orf6.Hygro (ECACC deposit no. P02041226). For the sake of clarity, the capital D stands for delta (Δ).

Disclosed are methods and means that solve certain difficulties related to diminished complementation of non-group C adenoviral vectors in Ad5-packaging/complementing cells. Although in the Ad5-complementing cell lines functional Ad5 E1B-55K expression is present, it was found that only very low titers of adenoviral vectors could be produced when the adenoviral backbone was of a non-group C adenoviral origin. This finding implies a serotype-specificity in the interaction of E1B-55K with another (viral) protein. It is herein disclosed that this serotype-dependency can be circumvented by providing E4-orf6 protein compatible with the E1B-55K protein provided by the complementing cell line. As discussed herein, E1B-55K and E4-orf6 form a complex that is involved in inhibiting transport of cellular mRNAs from the nucleus to the cytoplasm, while the complex is also involved in stimulation of transport of viral mRNAs from the nucleus to the cytoplasm. It has been observed by the present inventors that proper complementation of viral vectors in packaging cells requires the presence of E1B-55K and E4-orf6 gene products that are compatible. Packaging cells are also referred to as complementing cells if the cells comprise certain sequences encoding proteins that complement functions not provided by the vector that should be packaged. "Compatible," as used herein, therefore means that a complex between the available E1B-55K gene product is able to form a functional complex with the available E4-orf6 gene product in a sense that this protein complex supports viral replication, propagation and/or packaging to a level that is comparable to the wild-type situation or that is comparable to the situation found when a recombinant adenovirus serotype 5 vector is produced on a Ad5-complementing cell line such as 293 or PER.C6. Vector replication in packaging cells is efficient if, during the production period in which the virus is formed, the cell comprises at least an E1B-55K protein and an E4-orf6 protein that are compatible. Preferably, the E1B-55K and E4-orf6 sequences are from adenoviruses within the same adenovirus subgroup (such as A, B, C, D, E or F). More preferably, the E1B-55K and E4-orf6 sequences are from the same serotype. Since established cell lines are available in the art that are capable of supporting the growth of adenoviruses of subgroup C, such as serotype 5, it is even more preferred that the E1B-55K and E4-orf6 genes are derived from adenovirus serotype 5. As will be understood by one of skill in the art, compatibility may be determined in complementation tests or assays known by one of skill in the art of adenoviral vector production. The person of skill in the art will also understand that the invention can also be used for producing any adenovirus serotype on any complementing cell line as long as the E1B-55K and E4-orf6 proteins are compatible.

It has further been observed that the E4-orf6 gene product "matching" with the E1B in the complementing cell line can be provided by the adenoviral vector by replacing the E4-orf6 in the adenoviral vector of choice with an E4-orf6-encoding sequence that is compatible with the E1B gene present within the packaging cell line. This modification was surprisingly found not to have a severe effect on the stability, replication, packaging, assembly and production of the vector.

One is now able to efficiently produce adenovirus serotypes different from those of subgroup C on cell lines normally applied for producing adenovirus serotype 5 or other serotype from subgroup C, such as serotype 1, 2 and 6. Provided are methods for producing non-group C adenoviruses without the necessity of separately providing the complementing (packaging) cell with E4-orf6 because the E4-orf6 sequence that is compatible with the complementing E1B-55K sequence is incorporated in the adenoviral backbone.

Provided is a recombinant adenovirus vector comprising structural and non-structural elements of an adenovirus of a first serotype, wherein the vector further comprises a sequence encoding a functional E4-orf6 protein or a functional part, derivative and/or analogue thereof, wherein the sequence is selected from the group consisting of: a) an E4-orf6-encoding sequence derived from an adenovirus of a second serotype different from the first serotype; b) an E4-orf6-encoding sequence derived from an adenovirus of the first serotype comprising a deletion, mutation, addition and/or substitution in one or more codons; and c) an E4-orf6-encoding sequence comprising a fusion between a part of an E4-orf6-encoding sequence derived from a second serotype different from the first serotype and a part of an E4-orf6-encoding sequence derived from a third serotype, wherein the third serotype may be identical to or different from the first serotype. In certain embodiments, provided is a recombinant adenovirus vector according to the invention, wherein the first serotype and the second serotype are from different adenovirus subgroups. In certain embodiments, a recombinant adenovirus vector according to the invention is provided, wherein the first serotype is from a subgroup other than subgroup C and wherein the E4-orf6-encoding sequence is derived from an adenovirus serotype of subgroup C. More preferred is a recombinant adenovirus according to the invention, wherein the first serotype is from subgroup B and the second serotype is from subgroup C. More preferably, the E4-orf6-encoding sequence is derived from adenovirus serotype 5.

It has been recognized by those skilled in the art that different levels of neutralizing antibodies circulate in humans that are directed against different serotypes. It has been found that certain adenoviral serotypes encountered high titers of such neutralizing antibodies and that many individuals in different populations carried neutralizing antibodies against such serotypes. It was also found that certain serotypes were only neutralized in a minority of the samples (WO 00/70071). Apparently, certain serotypes from subgroup B were only neutralized in a small group of samples. Therefore, in certain embodiments of the invention, recombinant adenovirus vectors according to the invention are provided, wherein the first serotype is selected from the group consisting of adenovirus serotypes 11, 14, 16, 21, 34, 35 and 50. Highly preferred are recombinant adenoviral vectors, wherein the first serotype is serotype 11 or 35, while these encountered neutralizing antibodies only in a very small percentage of the tested samples.

The vectors of the invention can be used in different settings, such as gene therapy, functional genomics, tumor vaccination and/or antiviral vaccination. For this, it is necessary that the adenoviral vector functions as a gene delivery vehicle, wherein a non-native gene is incorporated into the adenoviral genome. The adenoviral particle can subsequently be targeted specifically to target cells of interest. The adenovirus binds to that specific cell either through capsid-receptor binding or through other means and delivers the transgene. Targeting of adenoviruses can be performed in many different ways. Persons of skill in the art of adenoviral vector targeting will be aware of all the different possibilities that are applied to deliver the adenoviral vectors to the cells of interest. Such possibilities include, but are not limited to, capsid alterations (fiber, hexon and/or penton modifications, such as deletions, swaps between fibers of different serotypes, and additions of peptides and/or other binding moieties), wherein chimeric fibers are produced that recognize a receptor present on the cell of interest, or wherein the binding of the penton base is utilized. Other possibilities are linking targeting moieties to the capsid proteins, wherein, for instance, binding peptides, known and strong binding proteins, or antibodies or parts thereof, are linked to the capsid proteins to achieve specific targeting. All such vectors can be produced using the methods and means provided by the invention. Therefore, the invention also discloses recombinant adenovirus vectors that further comprise a sequence encoding a non-adenoviral protein, polypeptide or peptide. Such sequences can be present on different locations within the adenoviral backbone, but preferably it is located in the E1 region, which is lacking in the recombinant adenoviral vectors of the invention. The E1 region is complemented by (the complementation) elements present in the complementing cells. The direction of the promoter, transgene and other regulatory sequences can be directed towards the left, as well as to the right, inverted terminal repeat.

The invention can also be used for producing viral vectors based on adenovirus and/or on other viruses such as the Adeno-Associated Virus (AAV), wherein the combination, such as an Ad-AAV chimeric virus, can integrate into the host cell genome. Several methods are known in the art for generating integrating adenoviruses. Generally, the invention is also useful for producing adenovirus forms that (specifically, or non-specifically) can integrate.

As mentioned, several non-adenoviral transgenes can be cloned into the recombinant adenoviral vectors of the invention. These do not only include regulatory nucleic acid sequences such as enhancers, promoters (e.g., strong non-adenoviral promoters such as the cytomegalovirus promoter, the SV40 promoter and the RSV promoter) and polyadenylation signals, but also heterologous genes for therapeutic purposes. Therefore, in one aspect of the invention, recombinant adenovirus vectors are provided, wherein the non-adenoviral protein, polypeptide or peptide is selected from the group consisting of: a cell death-inducing polypeptide, an antigenic determinant of a pathogenic organism, a tumor-specific antigen, a viral protein, a hormone and a cytokine. Examples of pathogenic organisms are, but are not limited to, bacteria, viruses and fungi. Non-limiting examples of non-adenoviral factors, proteins, polypeptides and peptides are transcription factors, intracellular signaling proteins, phosphatases, kinases, apoptosis-inhibiting factors, receptor antagonists, soluble forms of membrane-bound receptors, RNA inhibitors, anti-sense RNAs, decoy factors, ribozymes, and more specifically, thymidine kinase, erythropoietin, novel erythropoiesis-stimulating protein (NESP), IL3, ceNOS, gamma-interferon and gp 100. Non-adenoviral viral proteins can be cloned into the recombinant adenoviral vectors provided by the methods and means of the invention for vaccination purposes. Such viral proteins include, but are not limited to, gag, pol, env, nef, etc., for HIV vaccines, E6 and E7 proteins for Human Papilloma Virus vaccines, circumsporozoite proteins from *Plasmodium* protozoa for malaria vaccines, rotavirus components for rotavirus vaccines, ebola proteins for ebola vaccines, the F and G gene products from Respiratory syncytial virus (RSV) for RSV vaccines, HA and NA for influenza vaccines, etc.

The recombinant adenoviruses of the invention comprise structural and non-structural elements. Examples of structural elements are the genes encoding the capsid proteins, such as fiber, hexon and penton proteins, as well as the gene products itself. Examples of non-structural elements are the early genes that are expressed upon infection into a cell and that are down-regulated when the infection cycle proceeds. Other examples of non-structural elements are the genes encoding the proteins active during replication, such as pol and pTP. It is to be understood that the recombinant adenoviral vectors may comprise structural and non-structural elements derived from different serotypes. Examples of such vectors are, for instance, the adenoviral particles carrying chimeric fibers (see, WO 00/03029). Molecular biology techniques have made it possible to construct endless combinations of nucleic acid sequences. It is clear to a person of skill in the art of molecular biology that combining different sequences can be performed using different molecular techniques, such as polymerase chain reaction (PCR) as well as direct subcloning. Many of the sequences used in the invention, as well as sequences and chimeric constructs known in the art, are derived from different adenovirus serotypes. "Derived," as used herein, therefore means that such sequence combinations can be obtained through direct cloning from wild-type sequences obtained from wild-type viruses, while they can, for instance, also be obtained through PCR by using different pieces of DNA as a template. This also means that such sequences may be in the wild-type form, as well as in altered form. Another option for reaching the same result is through combining synthetic DNA. It is to be understood that "derived" does not exclusively mean a direct cloning of the wild-type DNA. A person skilled in the art will also be aware of the possibilities of molecular biology to obtain mutant forms of a certain piece of nucleic acid. These mutations may render a different functionality, but they may also be silent in a way that certain mutations do not alter the functionality of that particular piece of DNA and its encoded protein. Therefore, the terms "functional part, derivative and/or analogue thereof" are to be understood as equivalents of the nucleic acid they are related to. A person skilled in the art will appreciate the fact that certain deletions, swaps, (point) mutations, additions, etc., may still result in a nucleic acid that has a similar function as the original nucleic acid. It is, therefore, to be understood that such alterations that do not significantly alter the functionality of the proteins, such as the E4-orf6 and E1B-55K gene product, are within the scope of the invention.

Some alterations in the nucleic acid, such as a deletion, a mutation, addition and/or substitution in one or more codons may also significantly change the structure and/or functionality of the encoded gene product. The invention, therefore, also relates to E4-orf6-encoded sequences that are derived from the same adenovirus serotype as the backbone harboring the genes, for instance, the structural and non-structural elements, but wherein the E4-orf6-encoding sequence has been mutated such that it has become compatible with the E1 proteins (such as the E1B-55K gene product) present in the complementing cell in which the adenoviral vector is to be produced. The codon may be altered completely to change the encoded amino acid, but it may also be mutated partly to change the encoded amino acid. Deletions of nucleic acids may result in loss of one or more encoded amino acid, while it may also result in frame shifts. The invention also relates to E4-orf6 sequences present in the adenoviral nucleic acid that comprise different parts derived from different serotypes, wherein the domains that render the protein functional in compatibility may be used from one serotype, while the remainder of the E4-orf6 sequence or a part thereof is derived from another (un)related serotype (for instance, from the same subgroup, from different subgroups or from different species, or combinations thereof). It is, therefore, also within the scope of the invention to apply E4-orf6 fusion proteins that are compatible. Such fusion proteins may be the product of several pieces of nucleic acid.

A person of skill in the art will be aware of the fact that besides all human adenoviruses, numerous non-human adenoviruses have been identified in the art. Obviously, non-human adenoviruses can also be applied to reach the same results as disclosed by the invention. It will be clear to one of skill in the art that compatibility between E1B-55K and E4-orf6 may not be limited to human adenoviruses but that elements from adenoviruses specific for different species can also be compatible. Thus, it is also another aspect of the invention that non-human adenoviruses can be produced to high titers on known packaging cell lines available in the art as long as the E1B-55K and E4-orf6 gene products are compatible. Non-limiting examples of non-human adenoviruses that can be produced using the methods and means of the invention are canine, bovine, ovine, frog, porcine, equine, monkey and avian adenoviruses. "Serotypes," as used herein, therefore go beyond species-restricted serotypes. If, for instance, a monkey adenovirus E4-orf6 gene product is compatible with the E1B-55K provided by the packaging cell, then this combination is within the scope of the invention. Also, when fusions are applied between different serotypes or between E4-orf6 sequences derived from, for instance, a human and an avian adenovirus that is compatible with the E1B gene of the packaging cell, then that particular combination is also within the scope of the invention.

The invention provides a method for producing a recombinant adenovirus vector comprising structural and non-structural elements of an adenovirus of a first serotype, the method comprising the steps of: a) providing a complementing cell harboring an E1B-55K-encoding sequence or a functional part, derivative and/or analogue thereof, derived from an adenovirus of a second serotype in expressible form, with the necessary elements of an adenovirus such as to allow assembly of the recombinant adenovirus vector by the complementing cell, wherein the elements comprise at least some structural and non-structural elements from an adenovirus of the first serotype different from the second serotype and a sequence encoding a functional E4-orf6 protein or a functional part, derivative and/or analogue thereof, which is compatible with the expressible E1B-55K protein in the complementing cell; b) culturing the complementing cell in a medium under conditions allowing for production and assembly of the adenovirus vector to take place; and c) harvesting the recombinant adenovirus vector so produced from the medium and/or the complementing cell, wherein the sequence encoding the compatible E4-orf6 protein is present in the recombinant adenovirus vector so produced.

In certain embodiments, a method is provided wherein the E4-orf6-encoding sequence is selected from the group consisting of: a) an E4-orf6-encoding sequence derived from an adenovirus of the second serotype; b) an E4-orf6-encoding sequence derived from an adenovirus of a third serotype different from the first and second serotypes; c) an E4-orf6-encoding sequence derived from an adenovirus of the first serotype comprising a deletion, mutation, addition and/or substitution in one or more codons; and d) an E4-orf6-encoding sequence comprising a fusion between a part of an E4-orf6-encoding sequence derived from a third serotype and a part of an E4-orf6-encoding sequence derived from an adenovirus of the second serotype, wherein the third serotype may be identical to or different from the first serotype. In certain embodiments, the first and second serotypes are from different subgroups. In a more preferred embodiment, the second serotype is an adenovirus serotype of subgroup C. In an even more preferred embodiment, the second serotype is adenovirus serotype 5. In another particular aspect of the invention, the first serotype is an adenovirus serotype of subgroup B. Preferably, the first serotype is selected from the group consisting of adenovirus serotypes 11, 14, 16, 21, 34, 35 and 50.

There are several packaging cells known in the art that are used for complementing recombinant adenoviral vectors and to produce, assemble and package the adenoviral particles. Non-limiting examples of such cell lines are HEK-293, 911 and PER.C6™ cells. It is preferred to use cell lines that have already proven to deliver high titers of adenoviral stocks. Such cell lines express E1 proteins in a stable manner. It is, therefore, a preferred aspect of the invention to use cell lines and methods wherein the E1B-55K-encoding sequence is integrated into the genome of the complementing cell. More preferred, are complementing cells that are derived from a primary, diploid human cell or a progenitor cell thereof. Even more preferred, the complementing cell is derived from a primary human retinoblast cell, a primary human embryonic kidney cell, a primary human neuronal cell or a primary human amniocyte. Highly preferred is the use of a complementing cell in the methods provided by the invention, wherein the complementing cell is a PER.C6 cell or a derivative thereof. PER.C6 cells are well known in the art for not giving rise to replication-competent adenovirus when adenoviral DNA is used that has no overlap with the nucleic acid provided by the cells. Many of the adenoviral vectors used in the art lack the E1 region, therefore, in one aspect of the invention, the complementing cell comprises, integrated into its genome, a nucleic acid encoding at least one adenovirus E1A protein. Preferably, the nucleic acid encoding at least one adenovirus E1A protein is derived from an adenovirus serotype of a subgroup different than subgroup B. More preferably, the nucleic acid encoding at least one adenovirus E1A protein is derived from an adenovirus serotype of subgroup C. Highly preferred are embodiments wherein the nucleic acid encoding at least one adenovirus E1A protein is derived from an adenovirus serotype 5. In another embodiment of the invention, the invention provides a method, wherein the E4-orf6-encoding sequence and the E1B-55K-encoding sequence are derived from different adenovirus serotypes and wherein the different adenovirus serotypes are members of the same adenovirus subgroup. Preferably, the E4-orf6-encoding sequence and the E1B-55K-encoding sequence are derived from different adenovirus serotypes and wherein the different adenovirus serotypes are both members of subgroup C. More preferably, the E4-orf6-encoding sequence and the E1B-55K-encoding sequence are derived from the same adenovirus serotype. Highly preferred are methods, wherein the E4-orf6-encoding sequence and the E1B-55K-encoding sequence are derived from adenovirus serotype 5.

The invention also relates to a pharmaceutical composition comprising a recombinant adenoviral vector according to the invention or obtainable by a method provided by the invention. The pharmaceutical composition further comprises an acceptable pharmaceutical carrier, generally applied by one of skill in the art of preparation of pharmaceuticals. Furthermore, the invention relates to a method of treating a human body comprising administering to a human body a recombinant adenoviral vector, according to the invention, or a pharmaceutical composition provided by the invention. The invention also relates to methods in which adenoviral vectors can be produced using the proper complementing/packaging cells and the adenoviral vector of interest. For an efficient production process, it is useful to apply the correct cells with the proper adenoviral vector. Therefore, the invention also relates to a kit of parts comprising: a) a complementing cell for producing a recombinant adenovirus vector comprising structural and non-structural elements of an adenovirus of a first serotype, the cell harboring an E1B-55K-encoding sequence or a functional part, derivative and/or analogue thereof, derived from an adenovirus of a second serotype in expressible form; and b) on one or more replicable nucleic acid vectors all necessary adenoviral elements so as to allow assembly of the recombinant adenovirus vector by the complementing cell, wherein the elements comprise at least some structural and non-structural elements from an adenovirus of the first serotype different from the second serotype and a sequence encoding a functional E4-orf6 protein or a functional part, derivative and/or analogue thereof, which is compatible with the expressible E1B-55K protein in the complementing cell. Preferably, a kit of parts is used wherein the E4-orf6-encoding sequence is selected from the group consisting of: a) an E4-orf6-encoding sequence derived from an adenovirus of the second serotype; b) an E4-orf6-encoding sequence derived from an adenovirus of a third serotype different from the first and second serotypes; c) an E4-orf6-encoding sequence derived from an adenovirus of the first serotype comprising a deletion, mutation, addition and/or substitution of one or more codons; and d) an E4-orf6-encoding sequence comprising a fusion between a part of an E4-orf6-encoding sequence derived from a third serotype and a part of an E4-orf6-encoding sequence derived from an adenovirus of the second serotype, wherein the third serotype may be identical to or different from the first serotype.

The invention is particularly useful for the replication of E1-deleted chimeric adenoviruses that are derived almost entirely from a serotype other than adenovirus 5. Such vectors need only to be provided with a nucleic acid encoding adenovirus 5 E4-orf6 or a functional part, derivative and/or analogue thereof. Once provided therewith, the vector can be efficiently replicated on normal adenovirus 5 E1-complementing packaging cell lines. Stability of the vectors is improved and vectors may be complemented for deletions in both E1A and E1B. By providing such vectors with a nucleic acid encoding adenovirus E4-orf6, it is possible to enable efficient plaque purification and good yields in the absence of an additional wild-type contamination problem, when grown on 293 or 911 cells. In PER.C6, of course, wild-type adenovirus contamination can also be prevented in other ways.

An additional advantage of a recombinant vector of the invention is that there is no need to generate special cell lines in which adenovirus E4-orf6 is produced from a nucleic acid integrated into the genome. Although such cell lines exist, they are not easily maintained. This is at least in part due to the fact that with more and more foreign genes inserted into the genome of cell lines, it is difficult to maintain stability of all foreign sequences (or the expression thereof). In the invention, it was found that at least some of the problems associated with low yields of non-adenovirus serotype 5-based vectors and stability of adenovirus serotype vectors from subgroup B, such as adenovirus serotype 7, 11 and 35 on adenovirus serotype 5 packaging cell lines, can be overcome with a recombinant adenovirus vector of the invention.

EXAMPLES

Example 1

Generation of E1-Deleted Ad35 Viruses Expressing Ad5 E4-Orf6 on an Ad5-Complementing Cell Line The sequencing of the Adenovirus serotype 35 genome, as well as the construction of a plasmid-based vector system and generation of recombinant Ad35-based viruses, have been described in detail in WO 00/70071.

Figure 2:
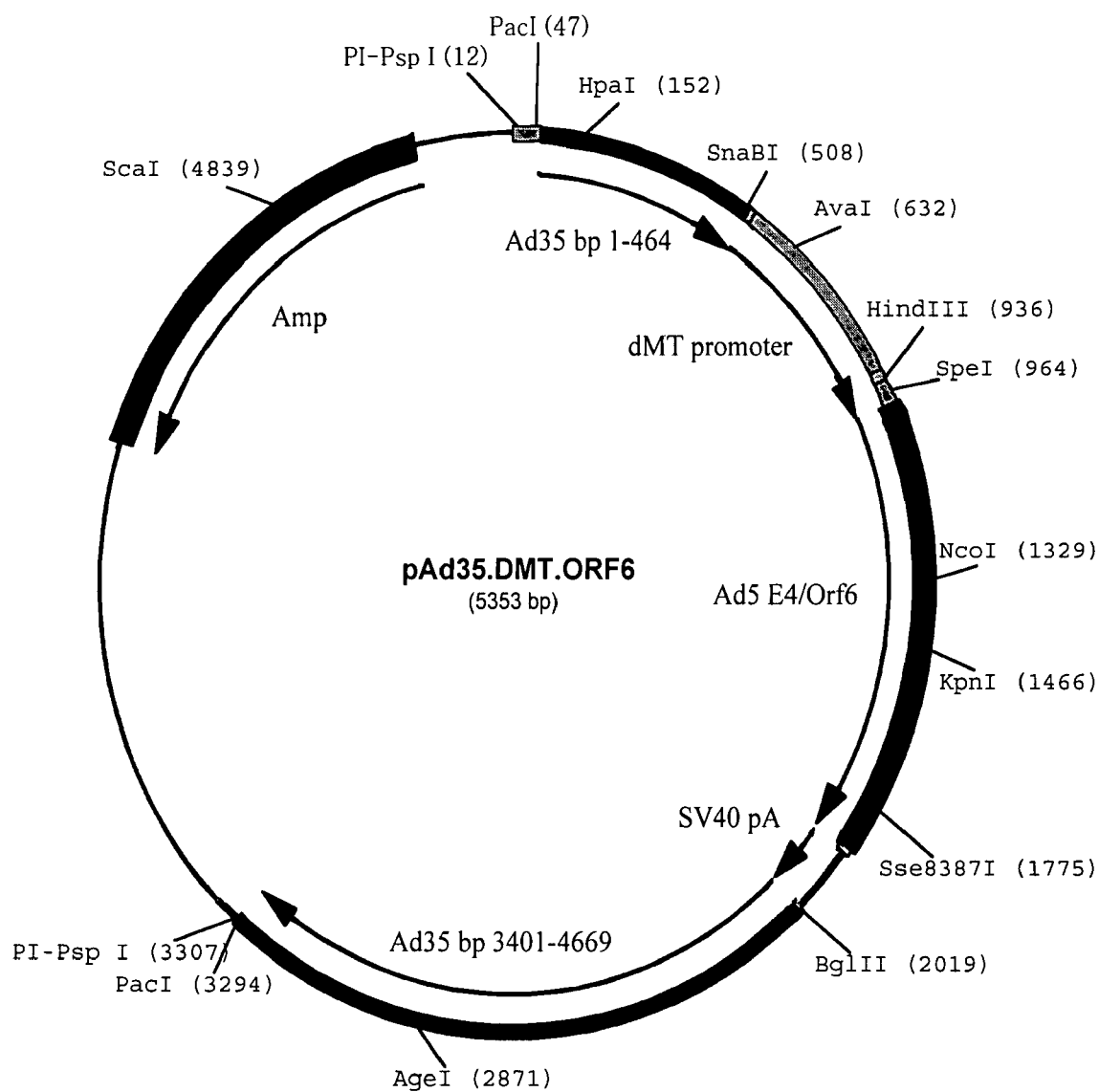
FIG. 2 is a schematic representation of plasmid pAd35.ΔMT.Orf6. For the sake of clarity, the capital D stands for delta (Δ).

The cloning of the Ad5 E4-orf6-coding sequence into pAdApt35IP1 (ECACC deposit no. P02041228, for cloning details of this plasmid, see WO 00/70071) was performed as follows. The plasmid was digested with NheI and AvrII and dephosphorylated with Calf Intestine Phosphatase (New England Biolabs). Digested DNA was isolated from gel using the GeneClean® kit (Qbiogene, Inc.). Plasmid pΔMT.Orf6.Hygro (FIG. 1, ECACC deposit no. P02041226) was digested with NheI and subsequently partially digested with XbaI. After separation of the resulting bands on gel, the 1350 bp fragment corresponding to the ΔMT promoter linked to the E4-orf6 sequence was purified from gel. Next, both isolated fragments were ligated and transformed into electrocompetent DH10B cells (Invitrogen/Life Technologies) after which a colony with the insert in the correct orientation with respect to the SV40 poly(A) signal was selected for large-scale DNA preparation. This resulted in construct pAd35.ΔMT.Orf6 (FIG. 2), which contained the Ad5 E4-orf6-coding sequence functionally linked to a mutated metallothionein promoter (ΔMT). The ΔMT promoter has been described by Hagmeyer et al. (1996). The Ad5 E4-orf6 sequence corresponds to nucleotide 33193 to nucleotide 34077 in the Ad5 sequence (GenBank accession number M73260). To test whether the expression of Ad5 E4-orf6 proteins would make production of fully E1-deleted Ad35 vectors possible on Ad5-complementing cells, pAd35.ΔMT.Orf6 was co-transfected with the Ad35 backbone construct pWE.Ad35.pIX-rITR onto PER.C6 cells. Hereto, pAd35.ΔMT.Orf6 was digested with PI-Psp-1 and pWE.Ad35.pIX-rITR was digested with NotI to liberate the adenoviral inserts from the backbone. Two µg of digested pAd35.ΔMT.Orf6 and 6 µg of digested pWE.Ad35.pIX-rITR were transfected using LipofectAmine™ (Invitrogen/Life Technologies). The transfection mixture was added to PER.C6 cells that were seeded the day before at a density of 3.5×10$^6$ cells per T25 flask. The next day, the medium was changed for PER.C6 culture medium (DMEM with 10% FBS and 10 mM MgCl$_2$) and cells were further incubated at 37° C./10% CO$_2$. Control transfections were performed with pAdApt35.Luc co-transfected with pWE.Ad35.pIX-rITR and pWE.Ad35.pIX-rITR alone. Two days after transfection, cells were passed from T25 to T80 flasks and incubated as described. Again, three days later, the culture transfected with pAd35.ΔMT.Orf6, together with the Ad35 backbone, showed cytopathogenic effect (CPE) indicative of virus replication and was harvested (including cells and medium) after a further incubation of two days. The cell suspension was subjected to two rounds of freeze/thaw cycles and the resulting material (crude lysate) was kept at −20° C. until further use. The other flasks did not show CPE and were passed 1:3 in T80 flasks six days after transfer to T80. Again, five days later, the pAdApt35.Luc+pWE.Ad35.pIX-rITR-transfected flask showed a few CPE-like events but this did not progress further. 0.2 and 0.5 ml of the crude lysate resulting from the pAd35.ΔMT.Orf6 transfection was used to re-infect PER.C6 cells at approximately 85% confluency in T80 flasks. This resulted in full CPE after one day of incubation, indicating that infectious virus was present in the crude lysates. These cultures were also harvested by two freeze/thaw cycles. Additional control transfections with construct pAd35.ΔMT.Orf6 alone onto PER.C6 were performed to confirm that orf6 expression by itself did not result in cell toxicity and CPE-like cell death. In conclusion, only the transfections with pAd35.ΔMT.Orf6, together with pWE.Ad35.pIX-rITR, did result in CPE and virus replication.

PCR analysis was performed to confirm the presence of Ad35-based viral genomes with Ad5-E4-orf6 replacing the former E1 region. Hereto, viral DNA was isolated from the crude lysate samples as follows. 275 µl of crude lysate material was incubated with 10 µl DNaseI (10 mg/ml) at 37° C. for 30 minutes. Subsequently, 6.0 µl 0.5 M EDTA (pH 8.0), 7.5 µl 20% SDS and 1.5 µl 20 mg/ml Proteinase K were added and mixed by vortexing. The mixture was then incubated at 50° C. for one hour. Finally, the viral DNA was isolated using the GeneClean® Spin Kit (Bio 101, Inc.). Two µl of the isolated DNA was then PCR amplified using primers 35 psi-For and 35R4 (Table 1). The program was set at 94° C. for two minutes, followed by 30 cycles at 94° C. for 30 seconds, 58° C. for 30 seconds, and 72° C. for five minutes, and ended by an incubation at 72° C. for ten minutes. The primers are specific for Ad35 sequences and generate a fragment of 2.9-kb ranging from the packaging sequence to nt 4669 (numbering as in wt Ad35 sequence), thus including the Ad5 orf6 transgene cassette. Electrophoresis of the obtained PCR fragments showed that the fragments had the expected length matching with the control PCR fragments generated on the adapter plasmid pAd35.ΔMT.Orf6. Thus, fully E1-deleted Ad35-based vectors can be made on Ad5-complementing cells if the virus also expresses Ad5-E4orf6.

Example 2

Construction of pWE.Ad35.pIX-rITR5E4

Figure 3:
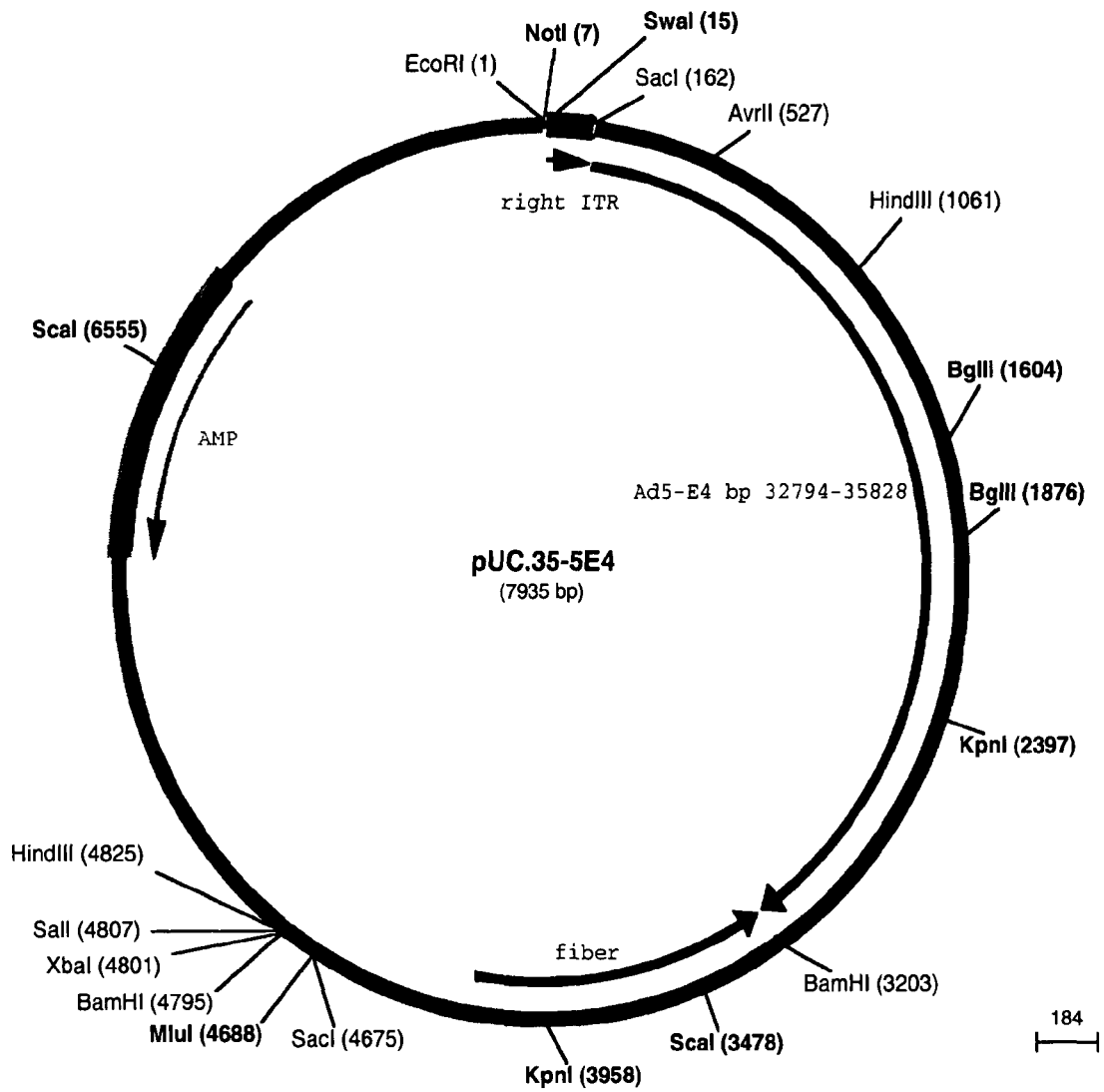
FIG. 3 is a schematic representation of pUC.35-5E4.
Figure 4:
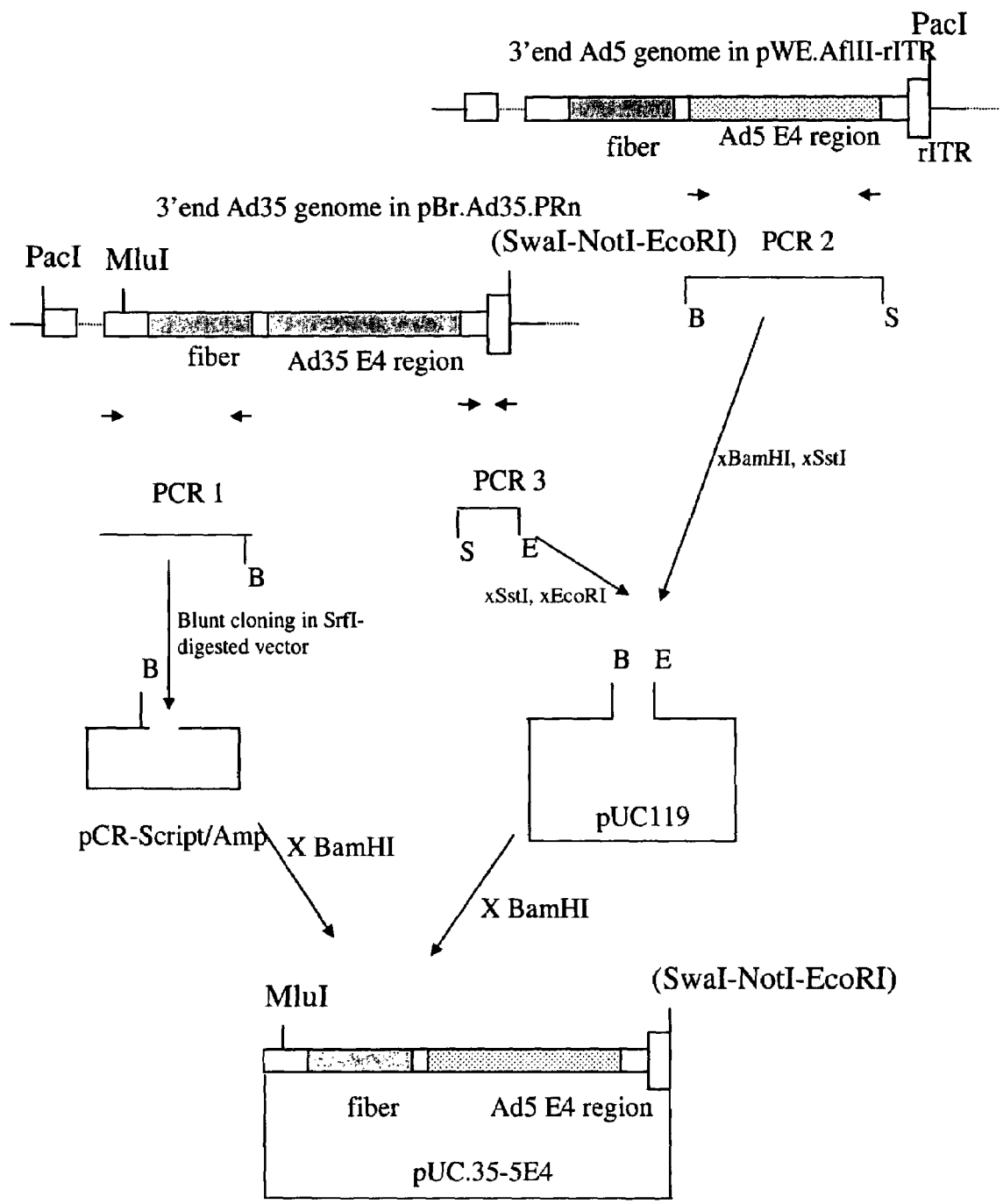
FIG. 4 is a representation of the cloning steps leading to pUC.35-5E4.
Figure 5:
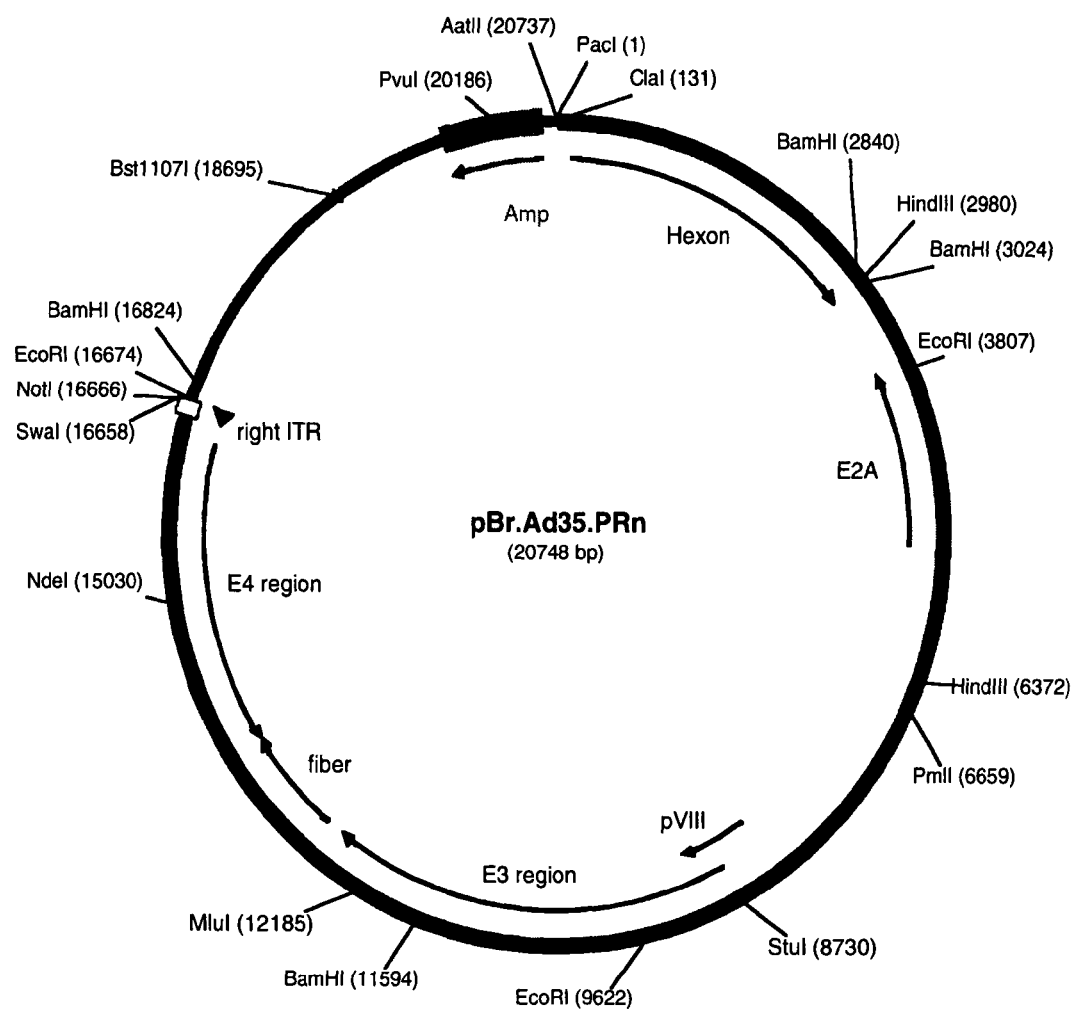
FIG. 5 is a schematic representation of pBr.Ad35.PRn.
Figure 6:
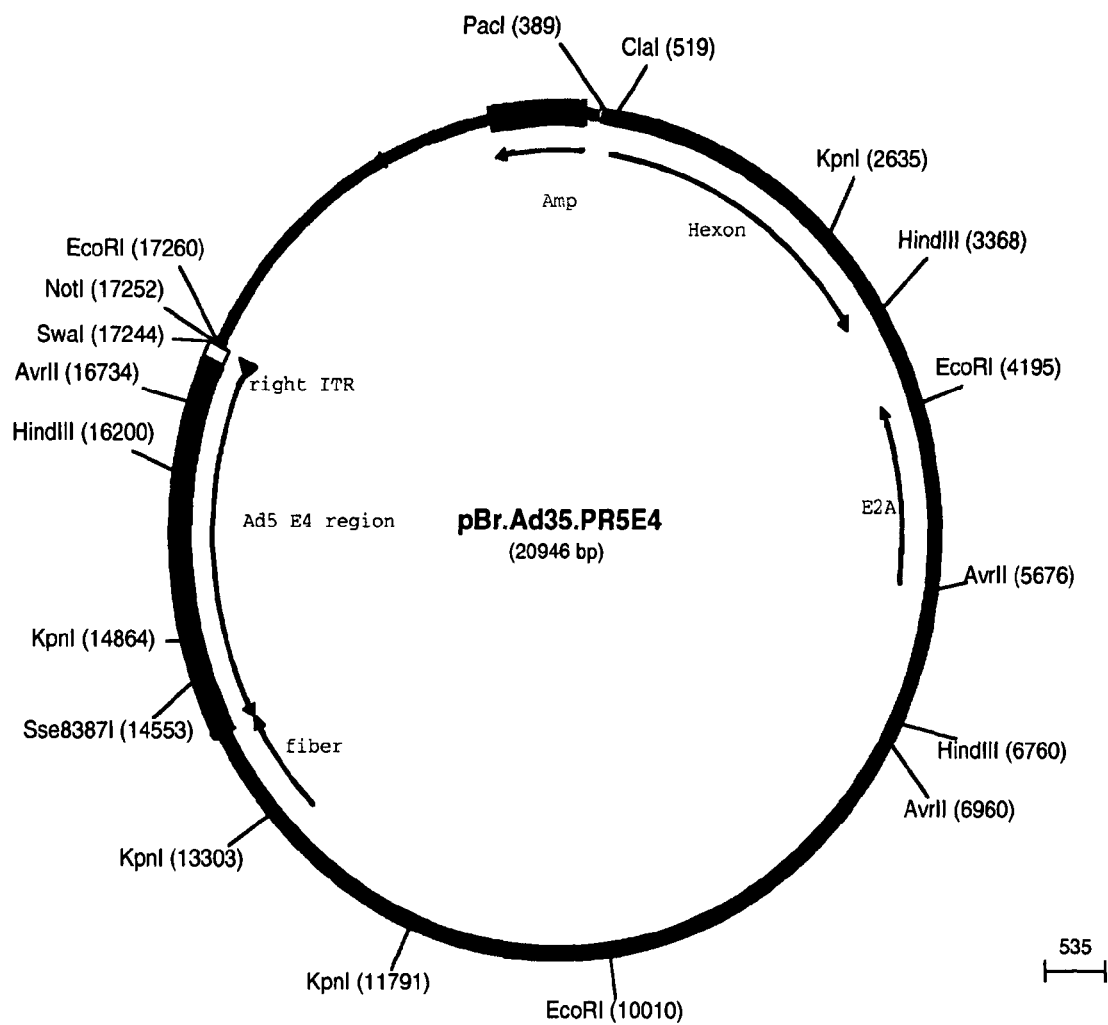
FIG. 6 is a schematic representation of pBr.Ad35.PR5E4 (ECACC deposit no. P02041229).
Figure 7:
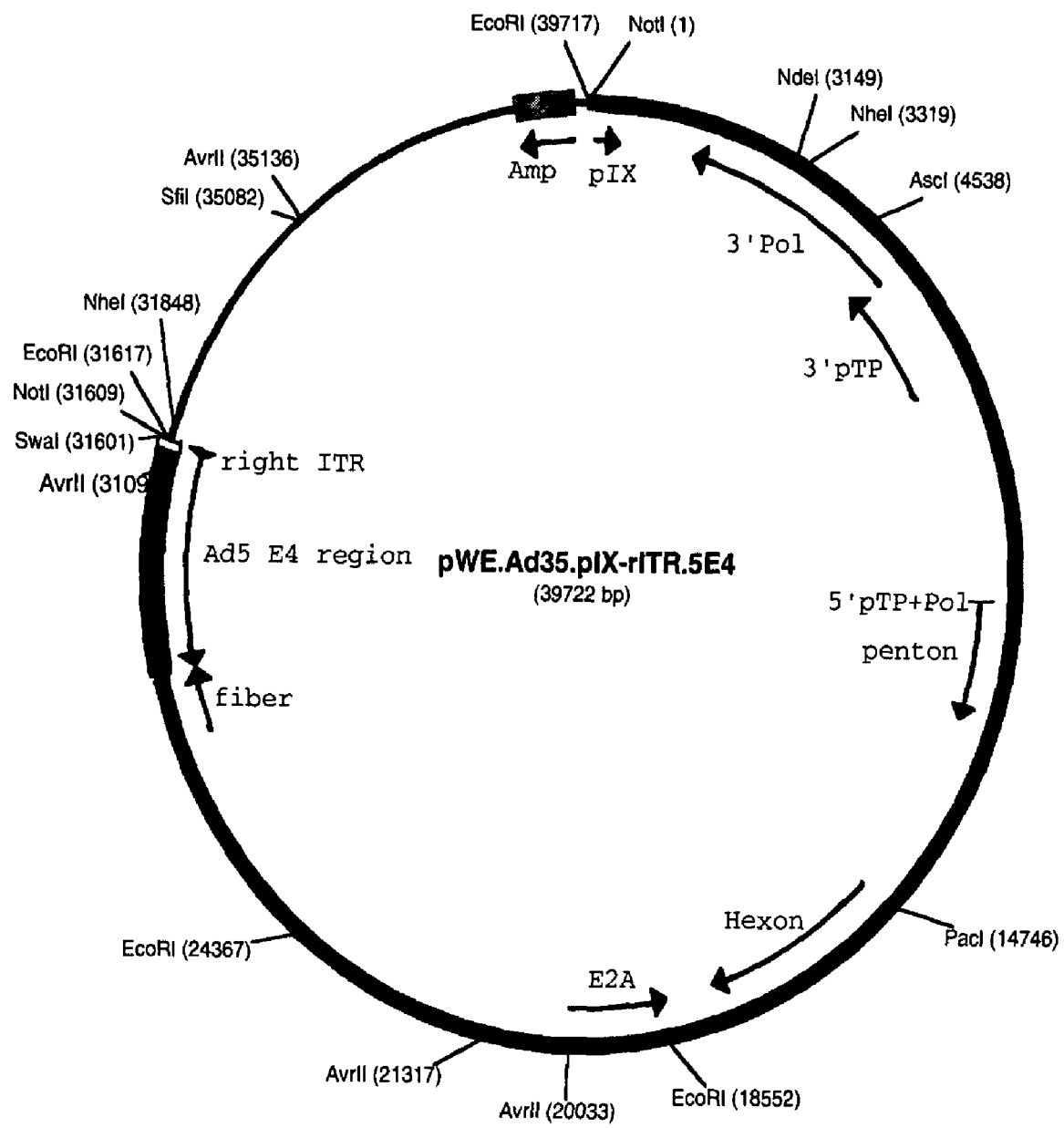
FIG. 7 is a schematic representation of pWE.Ad35.pIX-rITR.5E4.

A first PCR fragment was amplified using primers DF35-1 and 35FR (Table 1). Amplification was done with pWE.Ad35.pIX-rITR (see WO 00/70071) as template DNA using Pwo DNA polymerase (Roche) with additional DMSO (Sigma-Aldrich Co., final concentration 3%). The program was as follows: 94° C. for two minutes followed by 30 cycles at (94° C. for 30 seconds, 52° C. for 30 seconds, 72° C. for three minutes) and a final step at 72° C. for eight minutes to ensure complete fragments. Amplification resulted in a 1.6 kb fragment corresponding to nt 30224 to 31805 of the Ad35 sequence. A BamHI site was introduced at the 3' end. The amplified DNA was purified from gel using the GeneClean® kit (Qbiogene, Inc.) and ligated to the pCRScript/Amp cloning vector kit (Stratagene). Following transformation into electro-competent DH10B cells, white colonies were selected for further analysis. This resulted in construct pCR-fiber35. Due to the blunt cloning, the PCR fragment could be inserted in two orientations. A clone that had the insert with the BamHI site in the polylinker of the pCRScript/Amp vector at the 5' end was selected. Digestion with BamHI thus resulted in a 1.6 kb fragment. Sequencing confirmed correct amplification of the PCR fragment. A second PCR fragment was amplified using primers 5E4F and 5E4R (Table 1). Amplification was done with pWE.Ad5.AflII-rITRsp, which is a cosmid vector containing an extra PacI site in pWE.Ad5.AflII-rITR (ECACC deposit no. P97082116 described in applicant's international patent application PCT/NL01/00824). pWE.Ad5.AflII-rITRsp served as a template using Pwo DNA polymerase as described above, although pWE.Ad5.AflII-rITR could also be used for the same purpose. After purification from gel, the DNA was digested with SstI and BamHI (both sites introduced during the PCR) and the 3 kb fragment was purified from agarose gel using the GeneClean® kit (Qbiogene, Inc.). The Ad5 E4 region that is amplified corresponds to bp 32794 to bp 35828 of the Ad5 sequence. A third PCR fragment was generated on pWE.Ad35.pIX-rITR using primers 35SITR and 353ITR (Table 1). PCR amplification was performed as described above. The resulting 160 bp fragment is flanked by an SstI site (5' end) and an EcoRI site (3' end). After purification from gel as above, the DNA was digested with SstI and EcoRI. The 160 bp fragment corresponding to the right ITR of Ad35 was then separated from digested ends on a low melting-point agarose gel and collected in gel. Next, pUC119 was digested with BamHI and EcoRI and the 3.1 kb fragment was purified from gel using the GeneClean® kit (Qbiogene, Inc.). The above-treated second and third PCR fragments were then ligated with BamHI/EcoRI-digested pUC119 resulting in pUC.Ad5E4-35ITR. The cloned PCR-derived inserts were sequenced to verify correct amplification. Next, the 1.6 kb insert in pCR-fiber35 was excised with BamHI and the fragment was purified from gel as above. pUC.Ad5E4-35ITR was also digested with BamHI and the linear fragment was purified from gel. Ligation of both fragments and selection of the clones that had the correct orientation relative to each other resulted in pUC.35-5E4 (FIG. 3). The steps leading to the construction of pUC.35-5E4 are schematically represented in FIG. 4. The adenovirus insert in pUC.35-5E4 was subcloned into pBr.Ad35.PRn (FIG. 5; see WO 00/70071), a construct with Ad35 3' sequences. Hereto, construct pUC.35-5E4 is digested with MluI and NotI and the 4.7 kb fragment is purified from gel using the GeneClean® kit (Qbiogene, Inc.). This fragment is then ligated with the vector fragment resulting from MluI and NotI digestion of construct pBr.Ad35.PRn. This 16.3 kb fragment was purified from gel using agarase enzyme (Roche). Ligations were then transformed into competent DH10B cells. The resulting construct was named pBr.Ad35.PR5E4 (FIG. 6, ECACC deposit no. P02041229). The last step entails cloning of the modified 3' end of the Ad35 sequence into the viral cosmid clone pWE.Ad35.pIX-rITR. Hereto, two fragments are combined in a lambda phage packaging reaction (Stratagene) according to the manufacturer's instructions. The first is the 16.8 kb modified Ad35 insert from pBr.Ad35.PR5E4 obtained by digestion with PacI and SwaI and the second is a 22.8 kb fragment obtained by digestion of pWE.Ad35.pIX-rITR with PacI and SwaI. The correct combination of the two fragments yields pWE.Ad35.pIX-rITR.5E4 (FIG. 7). Thus, in this construct the E4 region in the Ad35 backbone is replaced with the corresponding region derived from Ad5.

Example 3

Construction of pWE.Ad35.pIX-rITR5Orf6

Figure 8:
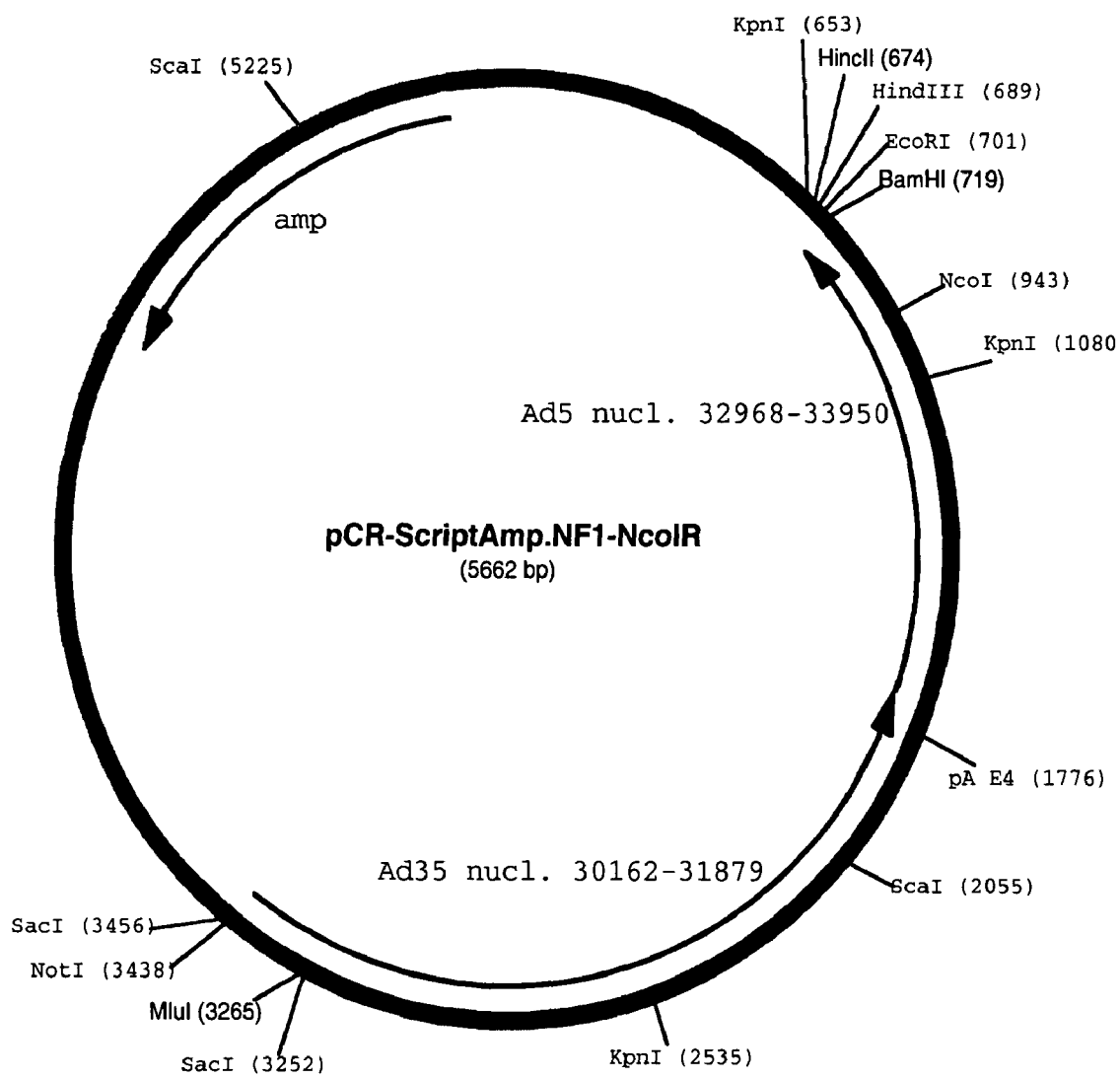
FIG. 8 is a schematic representation of pCR-scriptAmp.NF1-NcoIR.
Figure 9:
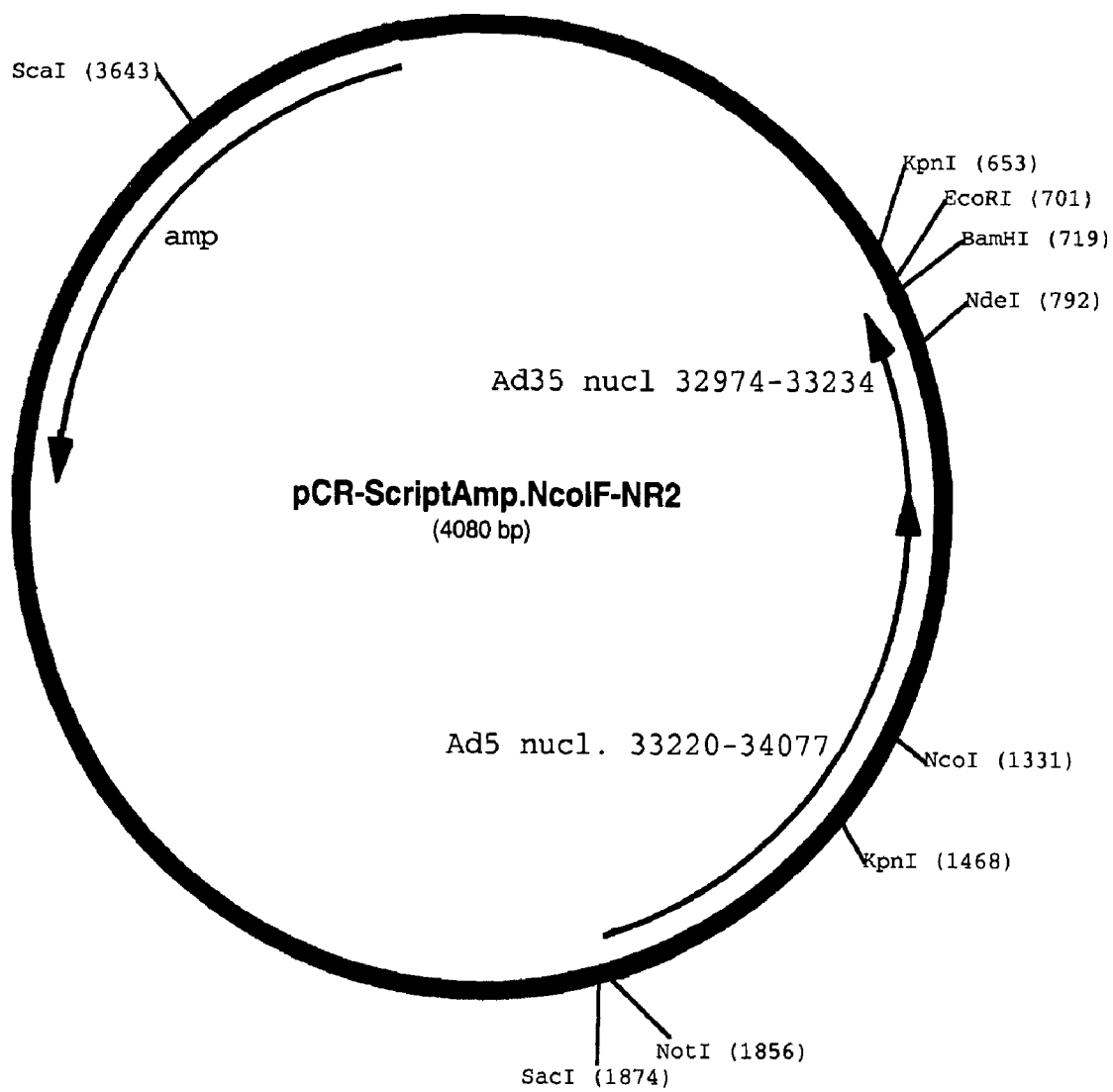
FIG. 9 is a schematic representation of pCRscriptAmp.N-coIF-NR2.
Figure 10:
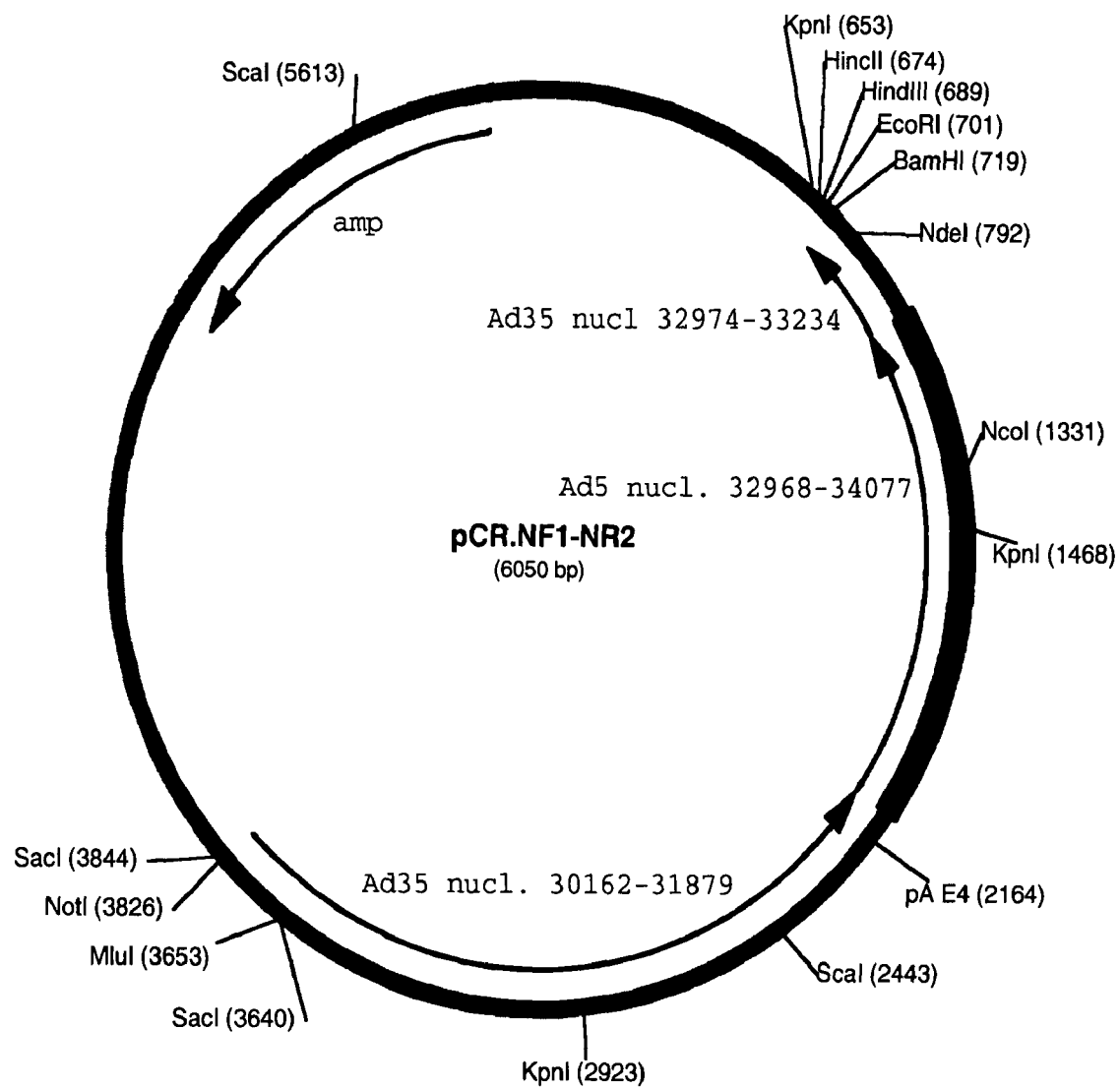
FIG. 10 is a schematic representation of pCR.NF1-NR2.
Figure 13:
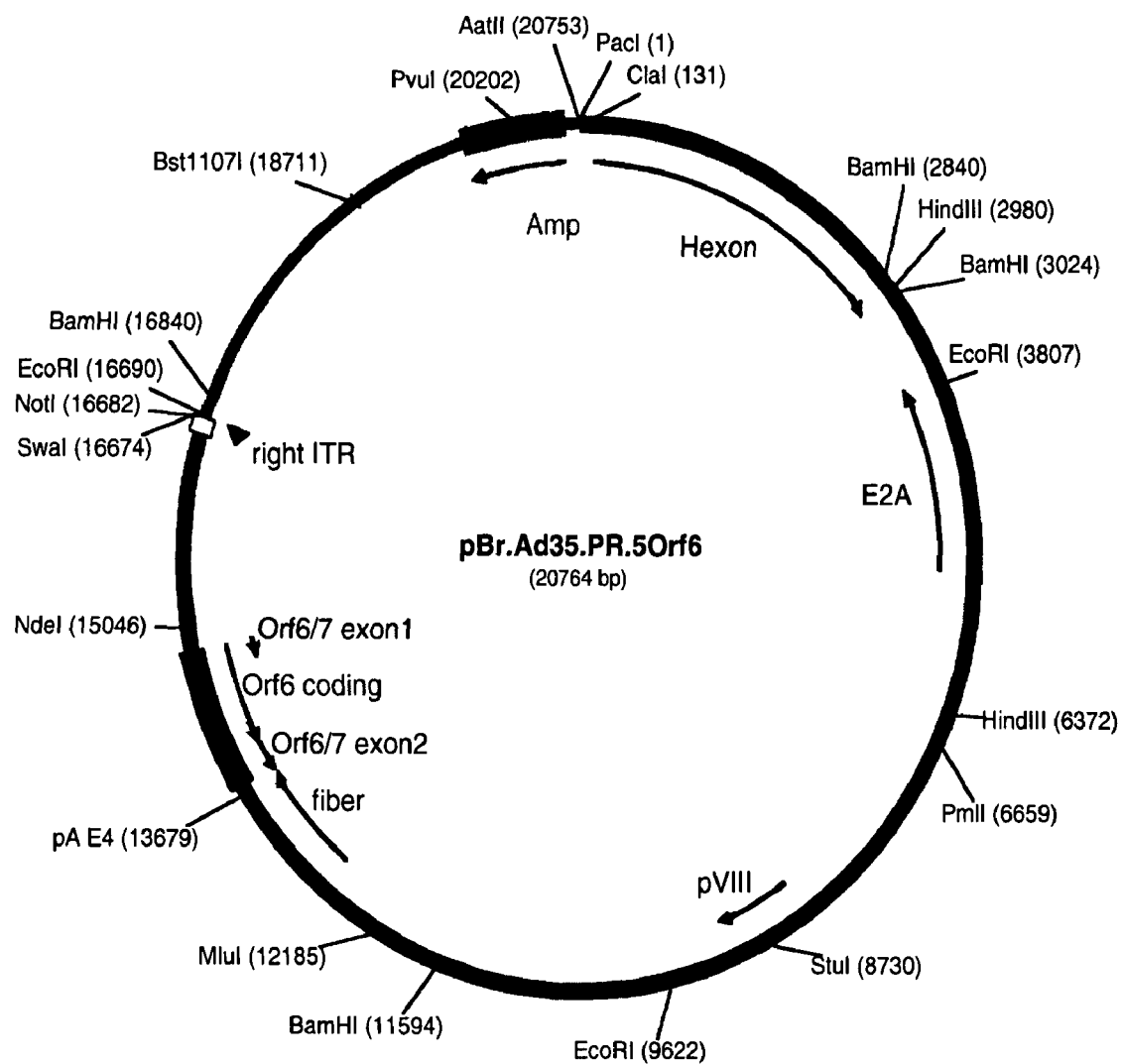
FIG. 13 is a schematic representation of pBr.Ad35.PR.5Orf6 (ECACC deposit no. P02041227).
Figure 14:
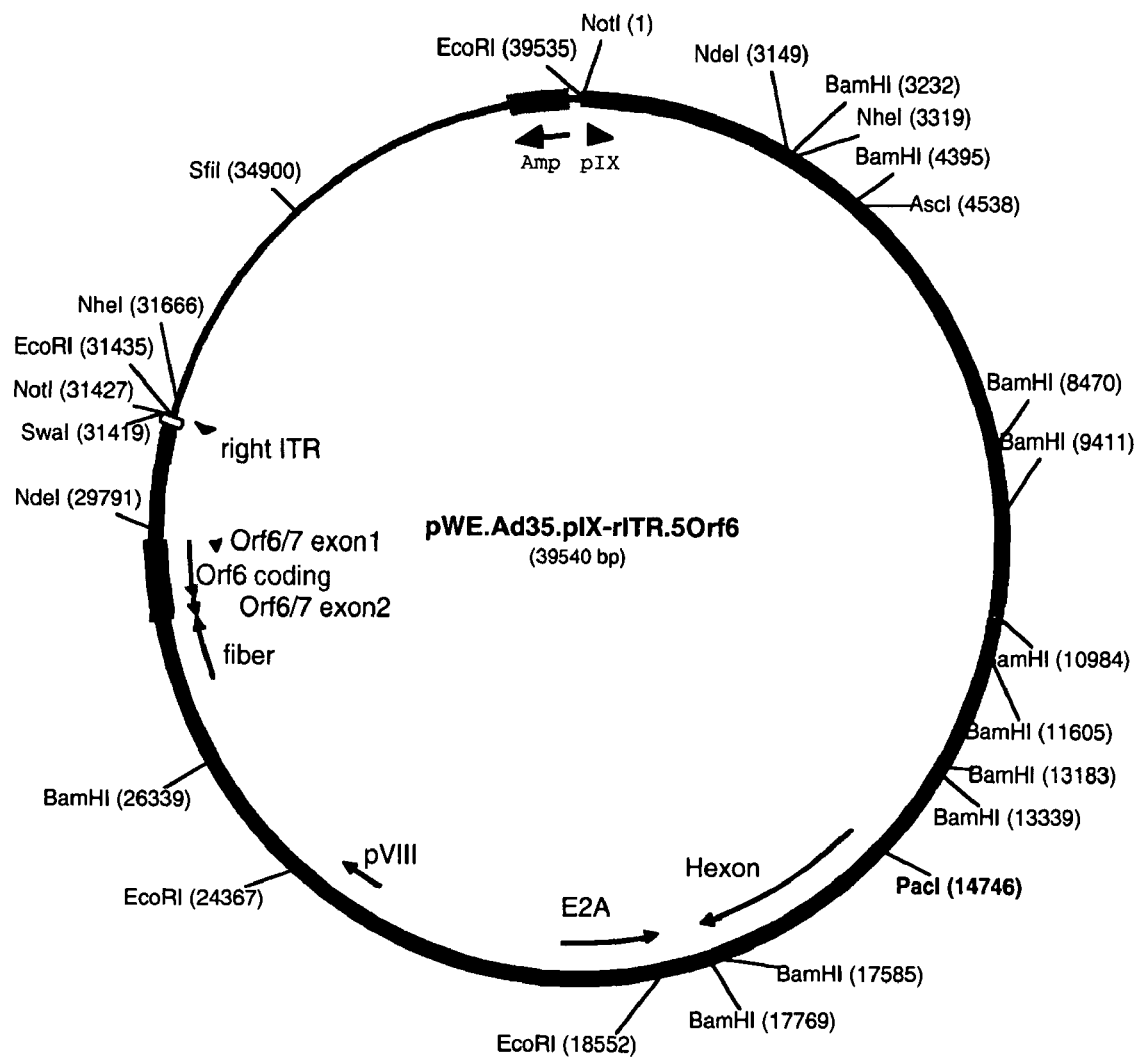
FIG. 14 is a schematic representation of pWE.Ad35.pIX-rITR.5Orf6.

To obtain an adenoviral backbone construct that contains the Ad35 sequences from the pIX gene (nt 3401 in the Ad35 sequence) to the end of the right ITR but with the sequences for E4-orf6 and -orf6/7 exchanged for the corresponding sequences of Ad5, Ad35 and Ad5 sequences were PCR amplified and combined as described below. PCR fragments were generated with Pwo DNA polymerase with addition of DMSO up to 3%. The first PCR was done with pBr.Ad35.PRn (FIG. 5; see WO 00/70071) as template and the primers E4-F1 and E4-R2 (Table 1). The program was set as follows: 94° C. for two minutes, five cycles at (94° C. for 30 seconds, 50° C. for 30 seconds and 72° C. for one minute) followed by 30 cycles at (94° C. for 30 seconds, 60° C. for 30 seconds and 72° C. for one minute) and ended with a final step at 68° C. for eight minutes. The resulting 1.8 kb fragment was purified using the GeneClean® kit (Qbiogene, Inc.). The second PCR was done with pWE.Ad5.AflII-rITRsp, which is a cosmid vector containing a PacI site in pWE.Ad5.AflII-rITR (ECACC deposit no. P97082116, described in applicant's international patent application PCT/NL01/00824, not yet published), as template and the primers E4-F3 and E4-R4 (Table 1). The program was set as follows: 94° C. for two minutes followed by 30 cycles at (94° C. for 30 seconds, 62° C. for 30 seconds and 72° C. for one minute) and ended with a final step at 68° C. for eight minutes. The 1.1 kb fragment was purified as above. The third PCR was done with pBr.Ad35.PRn as template and the primers E4-F5 and E4-R6 (Table 1). The program was set as follows: 94° C. for two minutes, five cycles at (94° C. for 30 seconds, 48° C. for 30 seconds and 72° C. for 45 seconds) followed by 30 cycles at (94° C. for 30 seconds, 56° C. for 30 seconds and 72° C. for 45 seconds) and ended with a final step at 68° C. for eight minutes. The 366 bp fragment was purified as above. Samples of the purified fragments were loaded on a gel to estimate the concentration and then the fragments were mixed together to contain 700 ng PCR-1, 650 ng PCR-2 and 430 ng PCR-3 in a total of 30 µl. To this mixture, 3 µl EcoPol buffer (New England Biolabs), 3 µl 2 mM dNTP solution and 3 µl milliQ H$_2$O was added. The resulting mixture was incubated at 94° C. for three minutes and then cooled down to 65° C. in a PCR machine at a rate of 0.5° C./second. Following incubation at 65° C. for ten minutes, the mixture was further cooled down to 20° C. at a rate of 0.050° C. per second and incubated for ten minutes at 20° C. Then 1 µl (5 units) Klenow enzyme (New England Biolabs) was added followed by an incubation of 60 minutes at 37° C. Five µl of this Klenow mixture was used as a template to separately amplify two fragments as follows. Primer set 1: NF-1 and NcoI-R (Table 1) was used in a reaction using Pwo DNA polymerase (Roche) with addition of DMSO to a final concentration of 3% and using the following settings of the PCR machine: 94° C. for two minutes followed by 30 cycles at (94° C. for 30 seconds, 66° C. for 30 seconds and 72° C. for three minutes) followed by a final incubation at 68° C. for eight minutes. Primer set 2: NcoI-F and NR-2 (Table 1) was used in a reaction using Pwo DNA polymerase (Roche) with addition of DMSO to a final concentration of 3% and using the following settings of the PCR machine: 94° C. for two minutes followed by 30 cycles at (94° C. for 30 seconds, 62° C. for 30 seconds and 72° C. for 90 seconds) followed by a final incubation at 68° C. for eight minutes. The resulting fragments of 2.7 kb (primer set 1) and 1.1 kb (primer set 2) were purified from gel using the GeneClean® kit (Qbiogene, Inc.) and each was ligated to the pCRscriptAmp vector (Stratagene) and transformed into DH10B electro-competent cells. This resulted in construct pCRscriptAmp.NFI-NcoIR (FIG. 8) and construct pCR-scriptAmp.NcoIF-NR2 (FIG. 9). Since the inserts contained blunt ends, two orientations were obtained of each cloning. Using KpnI digestions, the constructs with the orientation needed for further cloning were selected (see FIGS. 8 and 9). The inserts were then sequenced to verify correct amplification. Next, part of the insert from pCRscriptAmp-NcoIF-NR2 was excised using BamHI and NcoI and purified from gel as above. pCRscriptAmp-NFI-NcoIR was digested with the same enzymes and the vector-containing fragment was also purified from gel. Ligation of these fragments resulted in pCR.NF1-NR2 (FIG. 10). pCR.NF1-NR2 contained Ad35 sequences between nt 30162 and 33234 of the Ad35 sequence with E4-orf6 and E4-orf6/7 sequences between nt 31879 and 32974 replaced for Ad5-derived sequences located between 32968 and 34077 from the published Ad5 sequence in GenBank (Accession Number M73260). Thus, as can be seen in the amino acid alignments presented in FIGS. 11 and 12, the amino acid sequence of the cloned E4-orf6 protein is identical to the E4-orf6 sequence found in Ad5 and the E4-orf6/7 amino acid sequence is, for the greater part, identical to the E4-orf6/7 sequence present in Ad5. Obviously, different hybrid Ad35-Ad5 E4 constructs can be designed using the general method outlined above without departing from the invention. This chimeric insert from pCR.NF1-NR2 was then cloned into pWE.Ad35.pIX-rITR: pCR.NF1-NR-2 was digested with MluI and NdeI and the resulting 2.8 kb fragment was purified from gel using the GeneClean® kit (Qbiogene, Inc.). Construct pBr.Ad35.PRn was also digested with MluI and NdeI and the 18 kb vector fragment was isolated from gel using agarase enzyme (Roche). Ligation of both fragments resulted in construct pBr.Ad35.PR.5Orf6 (FIG. 13, ECACC deposit no. P02041227). The Ad35 sequences between PacI and SwaI containing the chimeric E4 region in this construct were then cloned into construct pWE.Ad35.pIX-rITR using lambda-phage packaging as described above. The resulting pWE.Ad35pIX-rITR.5Orf6 (FIG. 14) was then used to generate recombinant Ad35-based viruses by co-transfection on PER.C6 packaging cells with an Ad35 adapter plasmid.

Example 4

Construction of pWE.Ad35.pIX-rITRΔE3, pWE.Ad35.pIX-rITRΔE3.5E4 and pWE.Ad35.pIX-rITRΔE35Orf6

The Ad35 backbone was further modified by a deletion of E3 sequences. E3 proteins are known to modulate the host immune response to adenovirus infection and are, therefore, not necessary for in vitro propagation of recombinant viruses. Furthermore, the deletion of E3 sequences allows for insertion of larger heterologous sequences in the vectors without compromising the packaging efficiency. Also, for the application of adenoviral vectors as vaccination vehicles, expression of immunomodulatory genes encoded by the E3 region is not preferred. Methods for deleting E3 sequences in the pBr.Ad35.PRn plasmid (FIG. 5) are described below.

Figure 15:
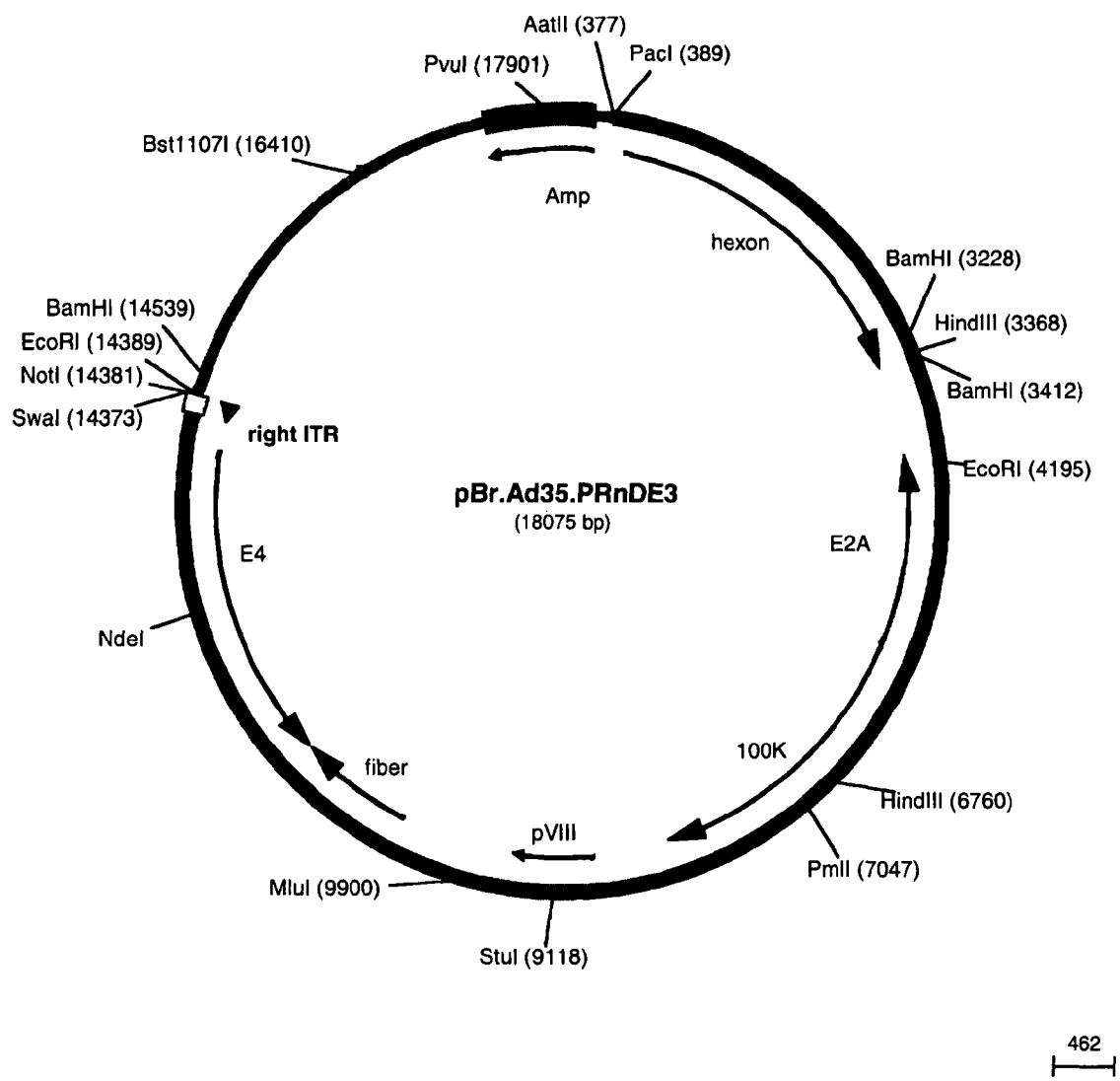
FIG. 15 is a schematic representation of pBr.Ad35.PRnΔE3. For the sake of clarity, the capital D stands for delta (Δ).

First, a PCR product was generated with primers 35E3for and 35E3rev (Table 1) using Pwo DNA polymerase (Roche) according to the manufacturer's instructions and pBr.Ad35.PRn as template DNA. The program was set at 94° C. for two minutes and 30 cycles at 94° C. for 30 seconds, 58° C. for 30 seconds and 72° C. for one minute, followed by 68° C. for eight minutes. The amplified fragment contained Ad35 sequences from nt 26814 to 27647 (see WO 00/70071) and was flanked at the 3' end by an MluI site. The resulting 833 bp fragment was purified using the Qiaquick PCR purification kit (Qiagen) and digested with MluI and StuI. The digested PCR fragment was then purified from an LMP agarose gel using the Qiaquick gel extraction kit (Qiagen). Construct pBr.Ad35.PRn was also digested with MluI and StuI and the 17.3 kb vector-containing fragment was isolated from agarose gel using agarase enzyme (Roche) using methods known to persons skilled in the art. Both isolated DNAs were ligated and transformed into Max-efficiency DH5α-competent bacteria (Invitrogen/LTI) to give pBr.Ad35.PRnΔE3 (FIG. 15). The deleted sequences encompass nt 27648 to 30320 of the Ad35 sequence resulting in a 2673 bp deletion. The E3 deletion was then introduced in construct pWE.Ad35.pIX-rITR using lambda-phage packaging extracts (Stratagene). Hereto, both pWE.Ad35.pIX-rITR and pBr.Ad35.PRnΔE3 were digested with PacI and SwaI and the respective 22.8 kb and 14 kb fragments were isolated from low melting-point agarose gels using agarase enzyme (Roche). After ligation and packaging using STBL-2 cells (Invitrogen/LTI), construct pWE.Ad35.pIX-rITRΔE3 was obtained.

Figure 16:
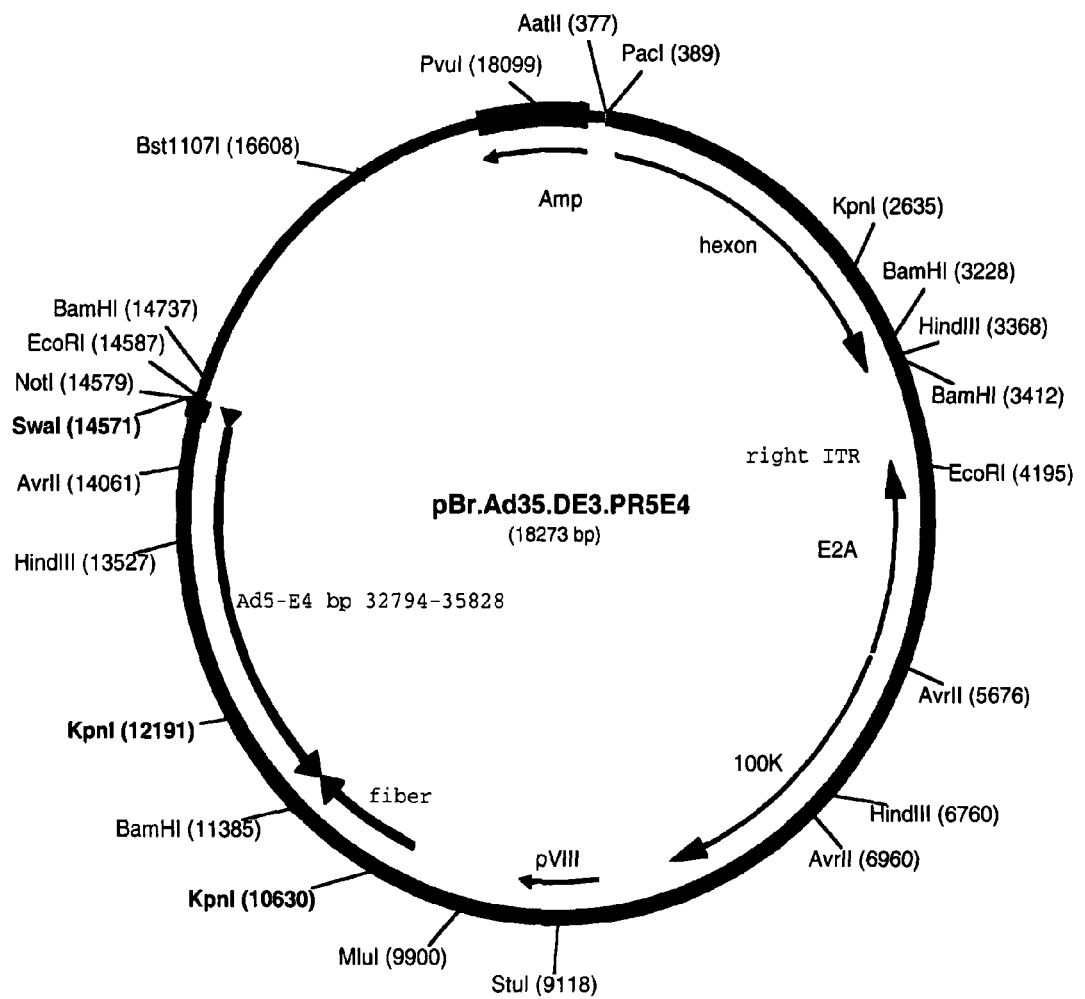
FIG. 16 is a schematic representation of pBr.Ad35.ΔE3.PR5E4. For the sake of clarity, the capital D stands for delta (Δ).
Figure 17:
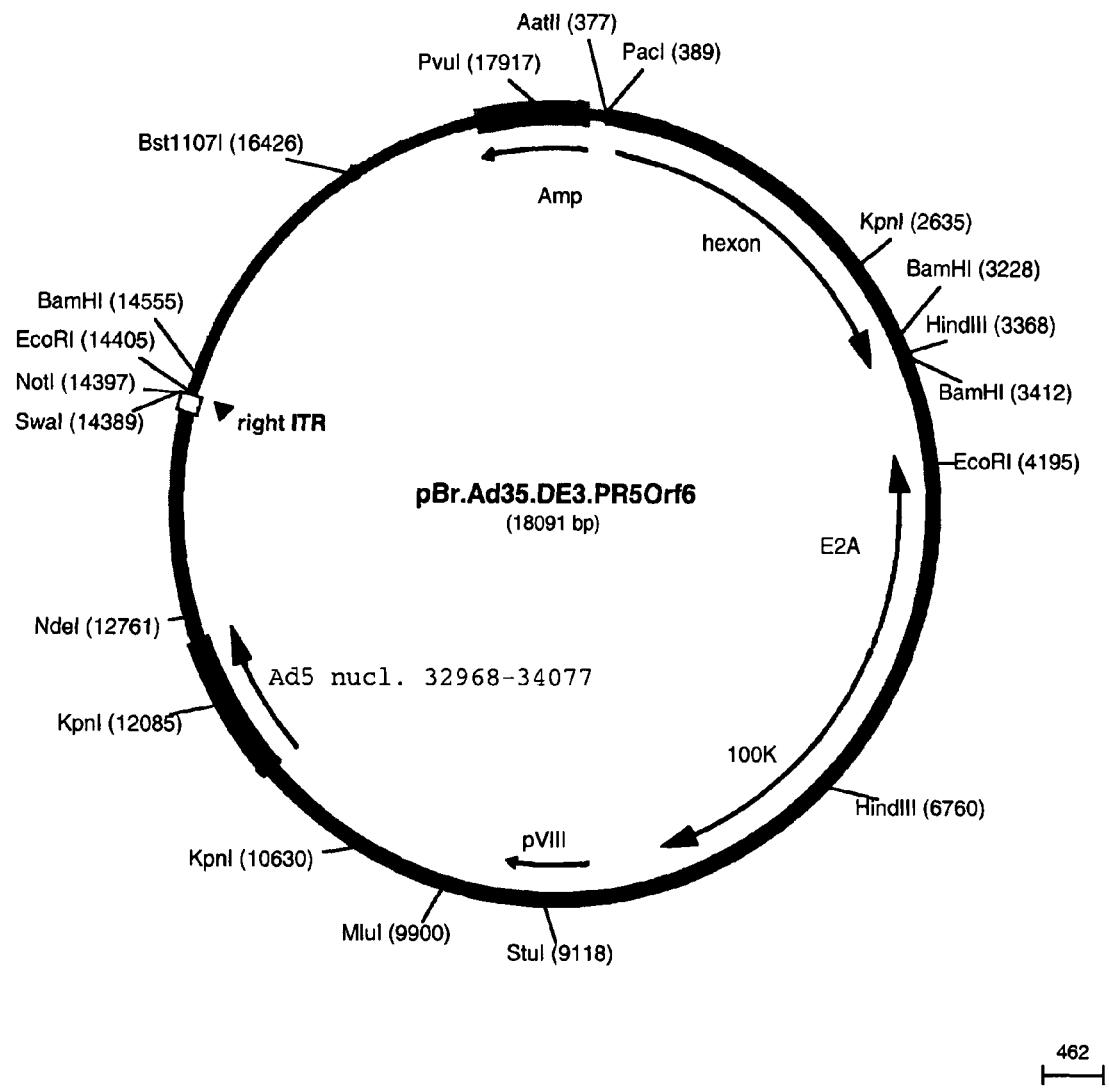
FIG. 17 is a schematic representation of pBr.Ad35.ΔE3.PR5Orf6. For the sake of clarity, the capital D stands for delta (Δ).

To construct the E3-deleted versions of the E4-modified backbone constructs described above, the E4 modifications were introduced into the pBr.Ad35.PRnΔE3 construct as follows. Construct pUC.35-5E4 (FIG. 3) was digested with MluI and NotI and the 4.7 kb fragment was isolated from gel using the GeneClean® II kit (Qbiogene, Inc.). Construct pBr.Ad35.PRnΔE3 was also digested with MluI and NotI and the 13.6 kb vector fragment was isolated from gel using the GeneClean® spin kit (Bio 101, Inc.). Ligation of these fragments resulted in construct pBr.Ad35.ΔE3.PR5E4 (FIG. 16). Construct pCR.NF1-NR2 (FIG. 10) was digested with MluI, NdeI and BglI (the latter to digest the vector fragment into smaller fragments), and the 2.8 kb fragment was isolated from gel using the GeneClean® spin kit (Bio 101, Inc.). Construct pBr.Ad35.PRnΔE3 was digested with MluI and NdeI, dephosphorylated using CIP enzyme (New England Biolabs) and the 15.2 kb vector fragment was also isolated using the GeneClean® spin kit (Bio 101, Inc.). Ligation of these fragments gave construct pBr.Ad35.ΔE3.PR5Orf6 (FIG. 17).

pBr.Ad35.ΔE3.PR5E4 and pBr.Ad35.ΔE3.PR5Orf6 were then used to swap the 3' PacI-SwaI fragment in pWE.Ad35.pIX-rITR for the corresponding regions from pBr.Ad35.ΔE3.PR5E4 and pBr.Ad35.ΔE3.PR5Orf6 as described, intra. This leads to constructs pWE.Ad35.pIX-rITRΔE3.5E4 and pWE.Ad35.pIX-rITRΔE3.5Orf6. An alternative method to generate these large cosmids is to use three fragments in the ligation reaction for packaging: a 14.7 kb NotI-PacI fragment from pWE.Ad35.pIX-rITR, the PacI-NotI insert from pBr.Ad35.ΔE3.PR5E4 or pBr.Ad35.ΔE3.PR5Orf6 and the NotI-digested pWE15 cosmid vector fragment (Stratagene). This latter fragment can also be isolated from the NotI/PacI digestion of pWE.Ad35.pIX-rITR.

Example 5

Generation of E1- and E1/E3-Deleted Ad35-Based Vectors on PER.C6 Cells

Figure 18:
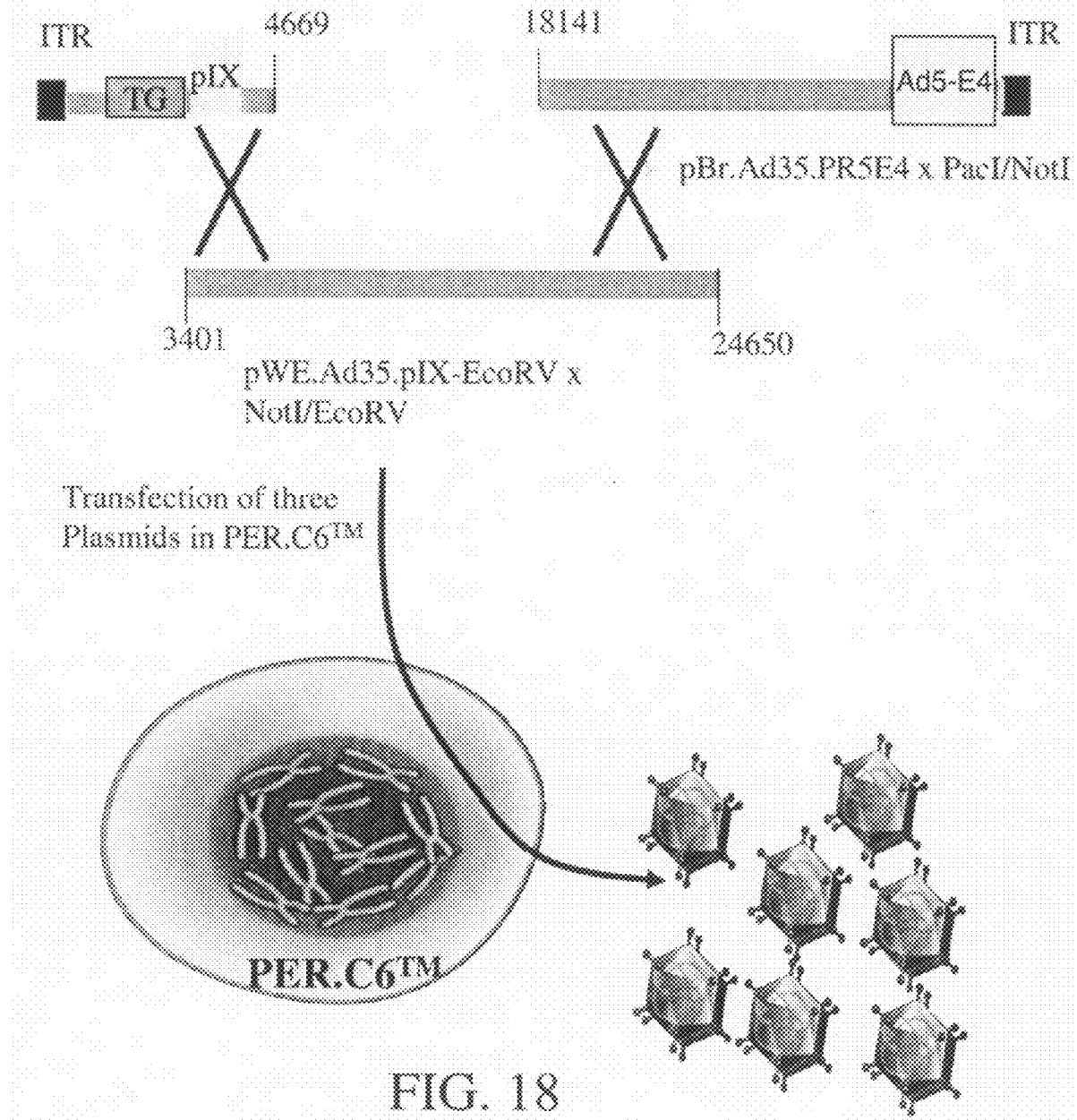
FIG. 18 shows the system for producing recombinant adenoviral particles in cells, such as PER.C6, through a double-homologous recombination event.
Figure 19:
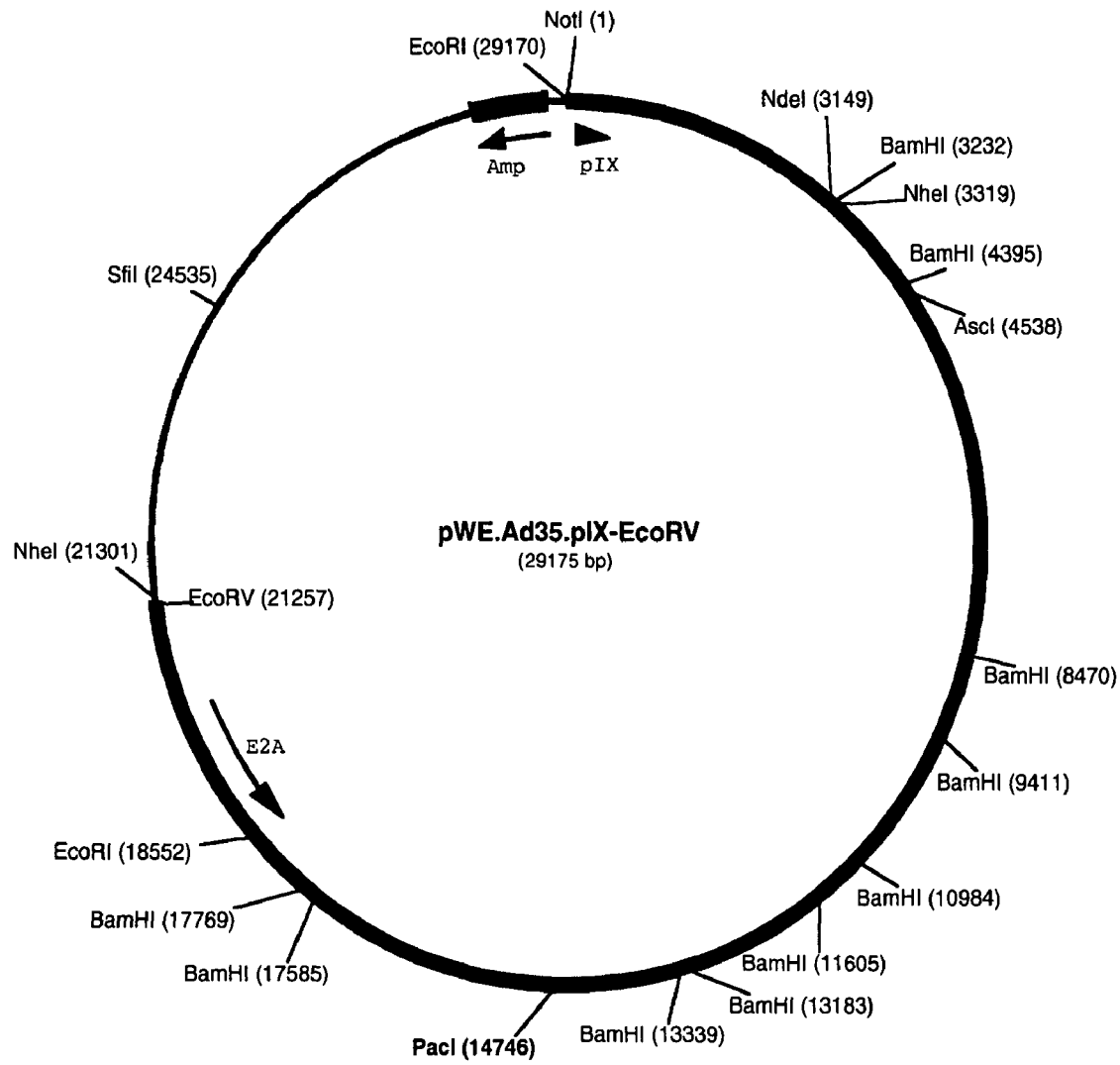
FIG. 19 is a schematic representation of pWE.Ad35.pIX-EcoRV.

To enable generation of recombinant Ad35 viruses on the complementing cell line PER.C6 using the pBr.Ad35.PRn-based constructs, we first made a new construct containing Ad35 sequences from bp 3401 to bp 24650 of the Ad35 sequence (WO 00/70071) and thus overlapping with both the adapter plasmids and the pBr.Ad35.PRn-based constructs. Transfection of these three plasmids into PER.C6 cells and a double-homologous recombination event leads to a complete viral genome and replication of recombinant viruses as outlined in FIG. 18. The required plasmid was made by deletion of a large part of the Ad35 sequences in pWE.Ad35.pIX-rITR. Hereto, pWE.Ad35.pIX-rITR was digested with EcoRV and the 29 kb vector-containing fragment was purified from a low melting-point gel using the Geneclean® spin kit (Bio 101, Inc.). The purified DNA was self-ligated and used to transform DH10B electro-competent bacteria (Invitrogen/LTI), resulting in pWE.Ad35.pIX-EcoRV (FIG. 19).

All DNAs used for transfection were digested as indicated in Table 2, heat-inactivated at 65° C. for 15 minutes and used without further treatment in the transfection. PER.C6 cells were seeded the day prior to transfection in T25 flasks at a density of 3×10$^6$ cells/flask and transfected as indicated in Table 2 using LipofectAmine (Invitrogen/LTI) according to the manufacturer's instructions, except that the transfection mixture in serum-free DMEM medium (Gibco/BRL) was replaced for PER.C6 culture medium (DMEM, 10% FBS and 10 mM MgCl2) after five hours. The day after, transfection efficiency was estimated at 50% by fluorescence microscopy. Two days later, cells were trypsinized and reseeded in T80 flasks and further incubated at 37° C./10% CO$_2$. Six days following transfection, all cultures showed full cytopathogenic effect (CPE, indicative for virus propagation) except for the PER.C6 culture transfected with Ad35.AdApt.eGFP+ pWE.Ad35.pIX-rITR. One day later, cells and medium in the flasks with CPE were harvested and subjected to two freeze/thaw cycles, clarified from cell debris by centrifugation (ten minutes at 1500 rpm) and 100 μl of these crude lysates were used to re-infect fresh PER.C6 cells at 85% confluency in T80 flasks. The transfection of Ad35.AdApt.eGFP+ pWE.Ad35.pIX-rITR that did not show signs of CPE was harvested by trypsinization and also treated as above. Two days following infection of fresh PER.C6 cells, all flasks showed full CPE except for the one that showed no signs of CPE at the time of initial harvesting. This clearly shows that fully E1-deleted Ad35-based viruses can be made on PER.C6 cells when the Ad5 E4-orf6 gene product is expressed from the Ad35 backbone.

TABLE 1

| | Primer sequences. |
|---|---|
| 35FR | 5'-CGGGATCCACTTTATTTTAGTTGTCGTCTTC-3' (SEQ ID NO: 1) |
| 3 5R4 | 5'-CGGAATTCTTAATTAAGGGAAATGCAAATCTGTGAGG-3' (SEQ ID NO: 2) |
| 35psi-For | 5'-GTGGTATTTATGGCAGGGTG-3' (SEQ ID NO: 3) |
| DF35-1 | 5'-CACTCACCACCTCCAATTCC-3' (SEQ ID NO: 4) |
| 5E4F | 5'-CGGGATCCGTTTGTGTTATGTTTCAACGTG-3' (SEQ ID NO: 5) |
| 5E4R | 5'-GCTGGCGAGCTCGGCGGAGTAACTTGTATGTG-3' (SEQ ID NO: 6) |
| 35SITR | 5'-GATCCGGAGCTCACAACGTCATTTTCCCACG-3' (SEQ ID NO: 7) |
| 3531TR | 5'-AGGAATTCGCGGCCGCATTTAAATC-3' (SEQ ID NO: 8) |
| E4-F1 | 5'-AGAGGAACACATTCCCCC-3' (SEQ ID NO: 9) |
| E4-R2 | 5'-GGGGAGAAAGGACTGTGTATTCTGTCAAATGG-3' (SEQ ID NO: 10) |
| E4-F3 | 5'-TTTGACAGAATACACAGTCCTTTCTCCCCGGCTGG-3' (SEQ ID NO: 11) |
| E4-R4 | 5'-ACAAAATACGAGAATGACTACGTCCGGCGTTCC-3' (SEQ ID NO: 12) |
| E4-F5 | 5'-GGACGTAGTCATTCTCGTATTTTGTATAGC-3' (SEQ ID NO: 13) |
| E4-R6 | 5'-TCACCAACACAGTGGGGG-3' (SEQ ID NO: 14) |
| NF-1 | 5'-CCACAACCCCCACTACTCCC-3' (SEQ ID NO: 15) |
| NR-2 | 5'-CGTCTCTTCCCTCTCCTCTCC-3' (SEQ ID NO: 16) |
| NcoI-R | 5'-AGGATCATCCGCTGCTGCCC-3' (SEQ ID NO: 17) |
| NcoI-F | 5'-CATCAGGATAGGGCGGTGG-3' (SEQ ID NO: 18) |
| 35E3for | 5'-AATGACTAATGCAGGTGCGC-3' (SEQ ID NO: 19) |
| 35E3rev | 5'-CGACGCGTTGTAGTCGTTGAGCTTCTAG-3' (SEQ ID NO: 20) |

TABLE 2

List of constructs used to generation E1-deleted Ad353-based viruses on PER.C6 cells as described in the examples. Adapter constructs were digested with PacI, pWE.Ad35.pIX-EcoRV was digested with NotI and EcoRV, E4-modified pBr-based constructs were digested with PacI and NotI.

| No. | Constructs | | | CPE |
|---|---|---|---|---|
| 1 | pAdApt35.eGFP | pWE.Ad35.pIX-EcoRV | pBr.Ad35.PR5E4 | Yes |
| 2 | pAdApt35.eGFP | pWE.Ad35.pIX-EcoRV | pBr.Ad35.PR5Orf6 | Yes |
| 3 | pAdApt35.eGFP | pWE.Ad35.pIX-EcoRV | pBr.Ad35.ΔE3PR5E4 | Yes |
| 4 | pAdApt35.eGFP | pWE.Ad35.pIX-EcoRV | pBr.Ad35.ΔE3.PR5Orf6 | Yes |
| 5 | pAdApt35.eGFP | pWE.Ad35.pIX-rITRxNotI | | No |
| 6 | pAdApt5.eGFP | pWE.Ad5.AflII-rITRxPacI | | Yes |

REFERENCES

Abrahamsen K., Kong H.-L., Mastrangeli A., Brough D., Lizonova A., Crystal R. and Falck-Pedersen E. (1997) Construction of an adenovirus type 7a E1A-vector. *J. Virol.* 11:8946-8951.

Fallaux F. J., Kranenburg O., Cramer S. J., Houweling A., Van Ormondt H., Hoeben R. C. and Van der Eb A. J. (1996) Characterization of 911: A new helper cell line for the titration and propagation of early region 1-deleted adenoviral vectors. *Hum. Gene Ther.* 7:215-222.

Fallaux F. J., Bout A., Van der Velde I., Van den Wollenberg D. J., Hehir K. M., Keegan J., Auger C., Cramer S. J., Van Ormondt H., Van der Eb A. J., Valerio D. and Hoeben R. C. (1998) New helper cells and matched early region 1-deleted adenovirus vectors prevent generation of replication-competent adenoviruses. *Hum. Gene Ther.* 9:1909-1917.

Francki R I B, Fauquet C M, Knudson L and Brown F. (1991) Classification and nomenclature of viruses. Fifth report of the international committee on taxonomy of viruses. *Arch. Virol. Suppl.* 2:140-144.

Graham F. O., Smiley J., Russell W. and Nairn R. (1970) Characteristics of a human cell line transformed by DNA from human adenovirus type 5. *J. Gen. Virol.* 36:59-72.

Hagmeyer B. M., Duyndam M. C., Angel P., De Groot R. P., Verlaan M., Elfferich P., Van der Eb A. J. and Zantema A. (1996) *Oncogene* 12:1025-1032.

Horwitz M. S. (2001) Adenovirus immunoregulatory genes and their cellular targets. *Virology* 279:1-8.

Leppard K. N. (1997) E4 gene function in adenovirus, adenovirus vector and adeno-associated virus infections. *J. Gen. Virol.* 78:2131-2138.

Leppard K. N. (1998) Regulated RNA processing and RNA transport during adenovirus infection. *Seminars in Virology* 8:301-307.

Pilder S., Moore M., Logan J. and Shenk T. (1986) The adenovirus E1B 55K transforming polypeptide modulates transport or cytoplasmic stabilization of viral and host cell mRNAs. *Mol. Cell. Biol.* 6:470-476.

Rao L., Debbas M., Sabbatini P., Hockenbery D., Korsmeyer S, and White E. (1992) The adenovirus E1A proteins induce apoptosis, which is inhibited by the E1B 19-kDa and Bcl-2 proteins. *Proc. Natl. Acad. Sci. USA* 89:7742-7746.

Russell W. C. (2000) Update on adenoviruses and its vectors. *J. Gen. Virol.* 81:2573-2604.

Shenk T. (1996) Adenoviridae: The viruses and their replication. *In Virology*, eds. Fields B. N., Knipe D. M. and Howley P. M. (Lippincott-Raven, New York) 2:2111-2148.

Van der Vliet P. C. (1995) Adenovirus DNA replication. In The molecular repertoire of adenoviruses II, eds. Doerfler W. and Böhm P. (Springer-Verlag, Berlin). *Current Topics in Microbiology and Immunology* 199/II:1-30.

Yew P. R. and Berk A. J. (1992) Inhibition of p53 transactivation required for transformation by adenovirus early region 1B protein. *Nature* 357:82-85.

What is claimed is:

1. A method for producing a recombinant adenovirus comprising a recombinant adenovirus genome comprising sequences encoding structural and non-structural elements of an adenovirus of a first serotype and sequences encoding an E4orf6 protein from an adenovirus of a second serotype wherein the first serotype is different from the second serotype, said method comprising the steps of:
   providing a complementing cell comprising an E1B-55K-encoding sequence from the adenovirus of the second serotype wherein the E1B-55K-encoding sequence is operably linked to expression control sequences,
   introducing into the complementing cell the recombinant genome
   wherein the sequence encoding E4orf6 from the adenovirus of the second serotype is operably linked to an expression control sequence, and wherein the recombinant genome does not comprise a sequence encoding a functional E4-orf6 protein from the adenovirus of said first serotype;
   culturing said complementing cell wherein the step of introducing comprises the cell in a medium under conditions allowing for production and assembly of the recombinant adenovirus to take place; and harvesting the recombinant adenovirus so produced from the medium and/or the complementing cell.

2. The method according to claim 1, wherein said first serotype and said second serotype are from different subgroups.

3. The method according to claim 1, wherein said second serotype is an adenovirus serotype of subgroup C.

4. The method according to claim 3, wherein said serotype of subgroup C is adenovirus serotype 5.

5. The method according to claim 1, wherein said first serotype is an adenovirus serotype of subgroup B.

6. The method according to claim 5, wherein said serotype of subgroup B is selected from the group consisting of adenovirus serotypes 11, 14, 16, 21, 34, 35 and 50.

7. The method according to claim 1, wherein said E1B-55K-encoding sequence is integrated into the genome of said complementing cell.

8. The method according to claim 1, wherein said complementing cell is an immortalized primary, diploid human cell.

9. The method according to claim 1, wherein said complementing cell is an immortalized primary human retinoblast cell, an immortalized primary human embryonic kidney cell, an immortalized primary human neuronal cell or an immortalized primary human amniocyte.

10. The method according to claim 1, wherein said complementing cell is a PER.C6 cell.

11. The method according to claim 1, wherein said complementing cell comprises, integrated into its genome, a nucleic acid encoding at least one adenovirus E1A protein.

12. The method according to claim 11, wherein said nucleic acid encoding at least one adenovirus E1A protein is from an adenovirus serotype of a subgroup different than subgroup B.

13. The method according to claim 11, wherein said serotype of a subgroup different than subgroup B is an adenovirus serotype of subgroup C.

14. The method according to claim 13, wherein said serotype of subgroup C is an adenovirus serotype 5.

15. The method according to claim 1, wherein the recombinant genome further comprises a sequence encoding a non-adenoviral protein or peptide.

16. The method according to claim 1, wherein the complementing cell is a 293 cell.

17. A method for producing a recombinant adenovirus comprising a recombinant adenovirus genome comprising sequences encoding structural and non-structural elements of an adenovirus of a serotype from a subgroup other than subgroup C and sequences encoding an E4orf6 protein from an adenovirus of a serotype from subgroup C, said method comprising:
   providing a complementing cell comprising an E1B-55K-encoding sequence operably linked to expression control sequences, wherein the E1B-55K-encoding sequence is from the adenovirus of the serotype from subgroup C,
   introducing into said complementing cell the recombinant genome
   wherein the sequence encoding E4orf6 from the adenovirus of the serotype from subgroup C is operably linked to an expression control sequence, and wherein said recombinant genome does not comprise a sequence encoding a functional E4-orf6 protein from the serotype from a subgroup other than subgroup C;
   culturing said complementing cell wherein the step of introducing comprises the cell in a medium under conditions so as to produce and assemble said recombinant adenovirus; and harvesting the recombinant adenovirus produced from the medium and/or the complementing cell.

18. The method according to claim 17, wherein the adenovirus of a serotype from subgroup C is adenovirus serotype 5.

19. The method according to claim 17, wherein the adenovirus of a serotype from a subgroup other than subgroup C is an adenovirus serotype of subgroup B.

20. The method according to claim 19, wherein said adenovirus serotype of subgroup B is selected from the group consisting of adenovirus serotypes 11, 14, 16, 21, 34, 35, and 50.

21. The method according to claim 17, wherein the E1B-55K-encoding sequence is integrated into the genome of the complementing cell.

22. The method according to claim 17, wherein the complementing cell is a PER.C6 cell or a 293 cell.

23. The method according to claim 17, wherein the recombinant genome further comprises a sequence encoding a non-adenoviral protein or peptide.

* * * * *